United States Patent [19]

Taverne et al.

[11] Patent Number: 5,196,434
[45] Date of Patent: Mar. 23, 1993

[54] HETEROCYCLE-SUBSTITUTED ALKYLAMINES COMPOUNDS

[75] Inventors: Thierry Taverne, Saint Martin les Boulogne; Isabelle Lesieur, Gondecourt; Patrick Depreux, Armentieres; Daniel H. Caignard, Paris; Béatrice Guardiola, Neuilly sur Seine; Gérard Adam, Le Mesnil le Roi; Pierre Renard, Versailles, all of France

[73] Assignee: Adir et Compagnie, Courbevoie, France

[21] Appl. No.: 765,959

[22] Filed: Sep. 26, 1991

[30] Foreign Application Priority Data

Sep. 26, 1990 [FR] France ................... 90 11866

[51] Int. Cl.$^5$ .................. C07D 221/20; A61K 31/44
[52] U.S. Cl. ........................ 514/278; 514/226; 514/250; 514/321; 514/367; 514/316; 514/6; 514/50; 514/90; 514/105; 546/16; 546/198; 548/141; 548/159; 548/165; 548/169; 548/173; 548/16; 548/221
[58] Field of Search ............ 546/16, 198; 548/165, 548/170, 173, 221; 514/278, 321, 369, 375

[56] References Cited

U.S. PATENT DOCUMENTS 5,132,305 7/1992 Lesieur et al. ............ 514/233.8

FOREIGN PATENT DOCUMENTS 0171702 7/1985 European Pat. Off. .
0174811 3/1986 European Pat. Off. .
0281309 9/1988 European Pat. Off. .

OTHER PUBLICATIONS

Life Sciences 49, p. 37; "Use of a Conflict Procedure in Pigeons to Characterize Anxiolytic Drug Activity: Evaluation of Activity", etc.
"The Pharmacological Basis of Therapeutics" by Goodman and Gilman, Eighth Edition (1990) p. 49.
J. Med. Chem. 30, 1166–1176 (1987).
Acta Ther. 13(2), 125–129 (1987).

*Primary Examiner*—John M. Ford
*Assistant Examiner*—Jyothsna Venkat
*Attorney, Agent, or Firm*—Gordon W. Hueschen

[57] ABSTRACT

Compound of general formula (I):

$$\begin{array}{c} R_1 \\ | \\ O=C-N \\ | \\ X-A \end{array} \text{-(arene)-} (CH_2-CH_2)_n-N\begin{array}{c}R_2 \\ R_3\end{array} \quad (I)$$

where $R_1$, $R_2$, $R_3$, n, X and A are defined in the description.

Medicinal products.

11 Claims, No Drawings

HETEROCYCLE-SUBSTITUTED ALKYLAMINES COMPOUNDS

The present invention relates to new heterocycle-substituted alkylamines, to a process for preparing these and to pharmaceutical compositions containing them.

A large number of heterocycle-substituted alkylamines containing a benzoxazolinone, benzothiazolinone or benzoxazinone unit have already been described.

The Applicant has now discovered new heterocycle-substituted alkylamines with a totally different chemical structure which possess the property of binding with a very high affinity to 5-$HT_{1A}$ serotoninergic receptors. This affinity is coupled with an excellent specificity and that renders them usable in the treatment of diseases of the serotoninergic system, and more especially depression, stress, anxiety and schizophrenia, at lower doses than the compounds of the prior art. This feature, combined with their low toxicity, renders the compounds of the invention usable with a great safety which is especially advantageous in view of the frailty of the populations at which this type of treatment is aimed.

More specifically, the present invention relates to the compounds of general formula (1):

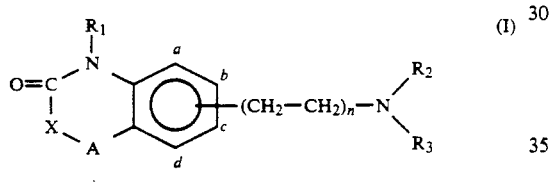

in which:

$R_1$ represents a hydrogen atom or a lower alkyl group, n represents 1 or 2,

A represents an oxygen or sulfur atom,

X represents a $CH_2$ group or a single bond, $R_2$ represents a hydrogen atom or a lower alkyl or lower acyl group while $R_3$ represents a group $(CH_2)pR_4$, with p an integer between 1 and 6, and $R_4$ represents:

either a nitrile group, and in this case $R_3$ represents a group $(CH_2)_{p-1}R_4$ or a halogen atom or an amino group optionally substituted with:
  a (lower alkyl)sulfonyl group,
  a phenylsulfonyl group optionally substituted on the phenyl ring with one or more lower alkyl, lower alkoxy, hydroxyl or trifluoromethyl groups or a halogen atom,
  one or two ($C_1$-$C_6$) acyl groups optionally substituted with a lower alkyl, lower alkoxy or hydroxyl group, a halogen atom or a phenyl, thienyl, benzothienyl, indolyl, furyl or benzofuryl group, the phenyl, thienyl, benzothienyl, indolyl, furyl and benzofuryl groups themselves optionally being substituted with one or more lower alkyl, lower alkoxy or hydroxyl groups or a halogen atom,
  one or two linear or branched ($C_1$-$C_6$) alkyl groups,
or $R_4$ represents any one of the following groups:

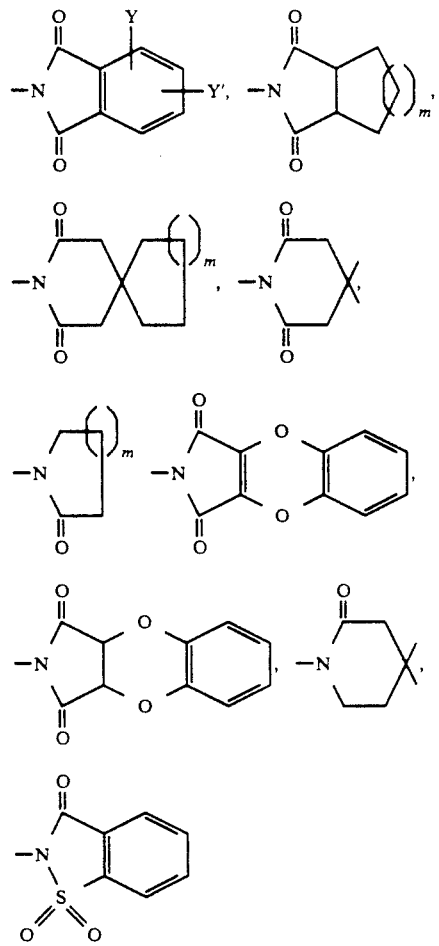

in which:

Y and Y', which may be identical or different, represent a hydrogen atom, a halogen atom or a lower alkyl, lower alkoxy or hydroxyl group, m is an integer equal to 1 or 2, their enantiomers, diastereoisomers and epimers as well as their addition salts with a pharmaceutically acceptable acid or a pharmaceutically acceptable base when $R_1 = H$.

Among pharmaceutically acceptable acids, hydrochloric, sulfuric, tartaric, maleic, fumaric, oxalic, methanesulfonic, camphoric, ethanesulfonic and citric acids, and the like, may be mentioned without implied limitation. Among pharmaceutically acceptable bases, sodium, potassium and calcium hydroxides, as well as sodium, potassium and calcium carbonates, and the like, may be mentioned without implied limitation.

The invention also encompasses the process for preparing the compounds of general formula (1), wherein a derivative of formula (II):

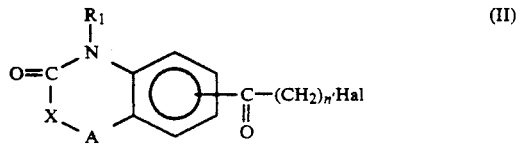

with Hal representing a halogen atom and $R_1$, A and X having the same definition as in the formula (I), and n' represents 1 or 3, is used as a starting material, which compound is treated with a trialkylsilane in an acid medium to yield a compound of formula (III):

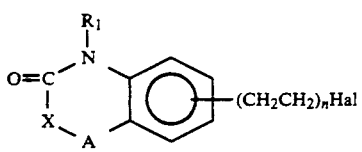
(III)

with A, X, R₁, n and Hal as defined above, which is condensed:
either with an amine of formula

(IV)

with R₂ and R₃ having the same definition as above, to yield a compound of formula (I):

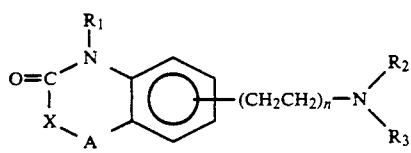
(I)

with R₁, X, A, n, R₂ and R₃ having the same definition as above, the isomers of which are separated, where appropriate, and purified if necessary by chromatography or crystallization,
or an amine of formula:

H₂NR₃   (IV/a)

in which R₃ has the same definition as above, to yield a compound of formula (I/a):

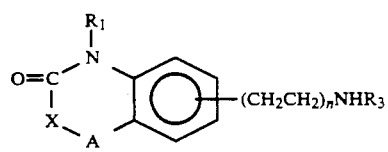
(I/a)

a special case of the compounds of formula (I), in which X, A, R₁, n and R₃ have the same definition as in the formula (I) and R₂ in this case represents a hydrogen atom, which is purified, if so desired, by chromatography and/or crystallization, the isomers of which are separated, where appropriate, and which is treated, if so desired, with a compound of formula (IV/b) in an alkaline medium:

Hal$_a$—R₂   (IV/b)

in which Hal$_a$ represents a halogen atom and R₂ has the same meaning as above, to yield a compound of formula (I), which is purified if necessary by chromatography and/or crystallization and the isomers of which are separated, where appropriate, which compound of formula (I) or (I/a), irrespective of the process according to which it has been obtained, may be, if so desired, salified with a pharmaceutically acceptable acid or The compounds for which R₃ = H may be used as intermediates in the synthesis of the compounds of formula (I). In this case, the compound of formula (I/a1)

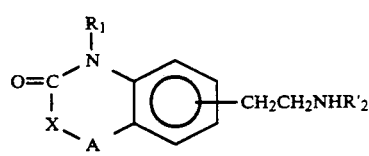
(I/a1)

where X, R₁ and A have the same definition as in the formula (I) and R'₂ represents a hydrogen atom or a lower alkyl group, or one of its addition salts with a pharmaceutically acceptable acid or, where appropriate, base, is treated
either with a compound of formula (V):

R₄—(CH₂)$_{p13}$ Hal'   (V)

in which Hal' represents a halogen atom and R₄ and p have the same definition as above, in the presence of an alkaline agent, to yield a compound of formula (I/b):

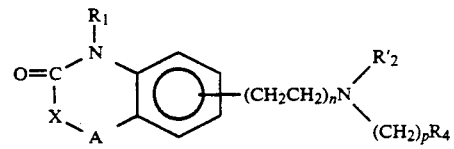
(I/b)

a special case of the compounds of formula (I) for which R₁, X, A, n, p, R'₂ and R₄ have the same meaning as above, the isomers of which compound of formula (I/b) are separated, where appropriate, which is purified, if so desired, by a technique of chromatography or of crystallization and which is treated, when R'₂ represents a hydrogen atom and R₂ a lower alkyl group, with a derivative of formula (VI):

R₂—Hal''   (VI)

in which R₂ has the same meaning as in the formula (I) and Hal'' represents a halogen atom, to obtain a compound of formula (I), the isomers of which are separated and which is purified if necessary by a technique of chromatography or of crystallization,
* either with a compound of formula (V) as defined above, to yield a compound of formula (1), which is purified if necessary by chromatography and/or crystallization after separation of the isomers, where appropriate,
* or with a compound of formula (VII):

Par—(CH₂)$_{p-1}$ Hal'''   (VII)

in which p has the same meaning as in the formula (I), Hal''' represents a halogen atom and Par represents either a CN group or a group CH₂Hal₄, where Hal₄ represents a halogen atom, to yield a compound of formula (I/d):

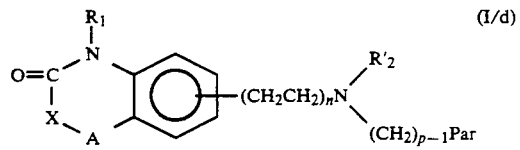
(I/d)

in which X, A, R₁, n, p, Par and R'₂ have the same definition as above, the isomers of which are separated, where appropriate, which is purified if necessary by chromatography and/or crystallization and which is treated, if so desired, either by catalytic hydrogenation or with an alkali metal mixed hydride in a $C_1$-$C_6$ aliphatic alcohol medium when Par represents a CN group, or with an excess of ammonia when Par represents a group CH₂Hal₄, where Hal₄ has the same definition as above, to yield a compound of formula (I/e):

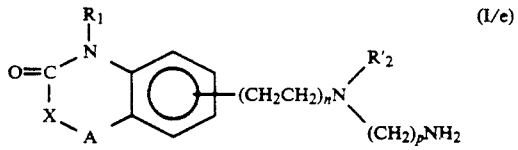

in which R₁, X, A, n, R'₂ and p have the same definition as above, the isomers of which are separated, where appropriate, which is purified, if so desired, by chromatography and/or crystallization and which is reacted with a compound of formula (VIII):

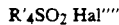

(VIII)

in which R'₄ is a lower alkyl group or a phenyl group optionally substituted with one or more lower alkyl, lower alkoxy, hydroxyl or trifluoromethyl groups or a halogen atom and Hal'''' is a halogen atom, to yield a compound of formula (I/f):

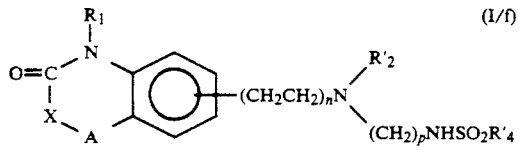

in which R₁, X, A, n, p, R'₂ and R'₄ have the as above, the isomers of which are separated, where appropriate, and which is purified if necessary by a technique selected from crystallization and/or chromatography, which compounds of formula (I/b), (I/d), (I/e) or (I/f), irrespective of the process according to which they have been obtained, may be salified by adding a pharmaceutically acceptable base or acid.

The compounds of formula (I) possess advantageous pharmacological properties.

Binding tests showed that the compounds of the invention behave as very potent ligands of 5-HT$_{1A}$ receptors. This affinity is accompanied by a very great selectivity with respect to other receptors, in particular D₂ and α₂, in contrast to the behavior observed with the compounds of the prior art.

The compounds of the invention are of low toxicity, and possess good activity in the pigeon conflict test, confirming the activity detected by binding. Some of them possess, moreover, an excellent analgesic activity, others a noteworthy hypnotic, antihypertensive or normolipemic activity.

The compounds of the invention hence find their application in the treatment of distress, anxiety, depression, schizophrenia, psychoses, dementia, senile dementia, aggressiveness and agitation, but also, for some of the compounds, in painful manifestations in all their forms, sleep disorders, arterial hypertension, glaucoma and the prevention of atheroma.

The subject of the present invention is also pharmaceutical compositions containing as active principle at least one compound of general formula (I) or one of its addition salts with a pharmaceutically acceptable acid or, where appropriate, with a pharmaceutically acceptable base, alone or in combination with one or more non-toxic, inert excipients or vehicles.

Among the pharmaceutical compositions according to the invention, there may be mentioned, more especially, those which are suitable for oral, parenteral or nasal administration, simple or sugar-coated tablets, sublingual tablets, sachets, packets, hard gelatin capsules, sublingual preparations, troches, suppositories, creams, ointments, skin gels, and the like.

The dosage varies according to the patient's age and weight and the nature and severity of the condition, as well as the administration route. The latter may be oral, nasal, rectal or parenteral.

Generally speaking, single doses range between 0.05 and 30 mg for conditions affecting mental behavior and between 1 mg and 500 mg for the treatment of pain and of arterial hypertension, that is to say, taken in one to three doses per 24 hours.

The examples which follow illustrate the invention and in no way limit the latter.

The 1H nuclear magnetic resonance spectra were recorded using TMS (tetramethylsilane) as an internal reference. The chemical shifts are expressed in parts per million (ppm). The infrared spectra were run in the form of a potassium bromide disk containing approximately 1% of the product to be analyzed.

The preparations do not form part of the invention, but are useful for carrying out the synthesis of the compounds of the invention.

PREPARATION 1

6-(BROMOACETYL)BENZOTHIAZOLINONE 210 g (1.60 mol) of aluminum chloride are introduced into a 500-cm³ ground-necked flask surmounted by a condenser, and 43 cm³ of dimethylformamide are then added dropwise and with magnetic stirring via a dropping funnel. 30.2 g (0.2 mol) of benzothiazolinone are then added and, while the reaction medium homogenizes, the temperature is stabilized at 70° C. using an oil bath. 19.8 cm³ (0.24 mol) of bromoacetyl chloride are then introduced gradually. After the addition, the mixture is left stirring for one hour at a temperature of 70° C. The reaction medium is hydrolyzed by pouring it onto crushed ice and the precipitate obtained is drained, washed copiously with water and dried. The product is recrystallized in dioxane.

Yield: 65%

Melting point 235° C. with decomposition

PREPARATION 2

6-(2-BROMOETHYL)BENZOTHIAZOLINONE

In a 500-cm³ ground-necked flask surmounted by a condenser, and placed in an oil bath, 40.8 g (0.15 mol) of 6-(bromoacetyl)benzothiazolinone are dissolved in 90 cm³ of trifluoroacetic acid with magnetic stirring and while the temperature is stabilized at 60° C. 52.7 cm³ (0.33 mol) of triethylsilane are introduced dropwise via a dropping funnel. After the addition, the heating is stopped and the mixture is then left stirring vigorously for 30 hours. The reaction medium is hydrolyzed by pouring it into ice-cold water, and the precipitate obtained is drained and washed with water until the filtrate is neutral and then with hexane. The product is dried and recrystallized in absolute ethanol.

Yield 80%

Melting point: 179°–180° C.

PREPARATION 3

3-METHYLBENZOTHIAZOLINONE

In a 2-liter flask, 75.6 g (0.5 mol) of benzothiazolinone are dissolved in a solution containing 20 g of sodium hydroxide (0.5 mol) in approximately 800 cm³ of water. The solution is filtered. With magnetic stirring, 47.5 cm³ of methylsulfate (0.5 mol) are introduced dropwise with a dropping funnel. After the addition, the mixture is left stirring for 20 hours at room temperature. The medium is alkalinized with a slight excess of sodium hydroxide and left stirring for one hour. The precipitate obtained is drained and washed with water until the filtrate is neutral. The product is dried. It is recrystallized in propanol.

Yield: 88%

Melting point: 72°–74° C.

PREPARATION 4

3-METHYL-6-(BROMOACETYL)BENZO-THIAZOLINONE 210 g (1.60 mol) of aluminum chloride are introduced into a 500-cm³ ground-necked flask surmounted by a condenser, and 43 cm3 of dimethylformamide are then added dropwise and with magnetic stirring via a dropping funnel. 33 g (0.20 mol) of 3-methylbenzothiazolinone are then added and, while the reaction medium homogenizes, the temperature is stabilized at 70° C. using an oil bath. 19.8 cm³ (0.24 mol) of bromoacetyl chloride are then added gradually. After the addition, the mixture is left stirring for one hour at a temperature of 70° C. The reaction medium is hydrolyzed by pouring it onto crushed ice and the precipitate obtained is drained, washed with water until the filtrate is neutral and dried. The product is recrystallized in 95° strength alcohol.

Yield: 66%

Melting point: 164°–165° C.

PREPARATION 5

3-METHYL-6-(2-BROMOETHYL)BENZO-THIAZOLINONE

In a 500-cm³ ground-necked flask surmounted by a condenser and placed in an oil bath, 42.9 g (0.15 mol) of 3-methyl-6-(bromoacetyl)benzothiazolinone are dissolved in 77 cm³ of trifluoroacetic acid with magnetic stirring and while the temperature is stabilized at 60° C. 52.7 cm³ (0.33 mol) of triethylsilane are introduced dropwise via a dropping funnel. After the addition, the heating is stopped and the mixture is left stirring vigorously for 30 hours. The reaction medium is hydrolyzed by pouring it into ice-cold water, and the precipitate obtained is drained and washed with water until the filtrate is neutral and then with hexane. The product is dried and recrystallized in cyclohexane.

Yield: 86%

Melting point: 97°–98° C.

PREPARATION 6

7-(BROMOACETYL)BENZOXAZINONE 0.01 mol of 7-acetylbenzoxazinone, described in Application EP 223,674, is dissolved in 100 cm³ of methylene chloride. 0.011 mol of bromine is added dropwise and with stirring via a dropping funnel, and stirring is maintained for 13 hours. The mixture is filtered and evaporated to dryness and the residue is recrystallized.

PREPARATION 7

6-(2-BROMOETHYL)-3-OXO-2,3-DIHYDRO-1,4-BENZOXAZINE

This product is advantageously obtained either by catalytic hydrogenation of 6-(bromoacetyl)-3-oxo-2,3-dihydro1,4-benzoxazine, described in French Patent Application 2,035,749, in an acetic acid medium in the presence of palladinized charcoal, or by the action of trialkylsilane on this compound in a trifluoroacetic acid medium.

PREPARATION 8

4-METHYL-7-(2-BROMOETHYL)-3-OXO-2,3-DIHYDRO-1,4-BENZOXAZINE 0.01 mol of 4-methyl-7-acetyl -3-oxo-2,3-dihydro-1,4-benzoxazine, obtained in European Patent Application 0,223,674, is dissolved in methylene chloride. 0.012 mol of bromine is added with stirring via a dropping funnel.

Stirring is maintained for two hours, and the reaction medium is then left in a oil bath at 40° C. with stirring for 2 hours. The mixture is filtered. The solvent is evaporated off. The residue is recrystallized.

The 4-methyl-7-(bromoacetyl)-3-oxo-2,3-dihydrobenzoxazine is converted to 4-methyl-7-(2-bromoethyl)-3-oxo-2,3-dihydro-1,4-benzoxazine by catalytic hydrogenation in an acetic acid medium in the presence of palladinized charcoal, or by the action of trialkylsilane in a trifluoroacetic acid medium.

PREPARATION 9

6-(2-PROPYLAMINOETHYL)-3-OXO-2,3-DIHYDRO-1,4-BENZOXAZINE

In a round-bottomed flask equipped with a mechanical stirrer and a calcium chloride guard tube, 0.01 mol of n-propylamine and 0.015 mol of triethylamine are added to a solution of 6-(2-bromoethyl)-3-oxo-2,3-dihydro-1,4-benzoxazine in 40 cm³ of dimethylformamide. The mixture is heated to reflux for 15 hours and the precipitate formed is drained in the heated state. The residue is evaporated under vacuum and the product is recrystallized.

PREPARATION 10

6-(4-BROMOBUTYL)BENZOTHIAZOLINONE

Using the procedure described in Preparation 2, but replacing 6-(bromoacetyl)benzothiazolinone by 6-(4-bromobutyryl)benzothiazolinone, the product of the title is obtained.

PREPARATION 11

3-METHYL-6-(4-BROMOBUTYL)BENZO-THIAZOLINONE

Using the procedure described in Preparation 5, but replacing 6-(bromoacetyl)-3-methylbenzothiazolinone by 3-methyl-6-(4-bromobutyryl)benzothiazolinone, the product of the title is obtained.

PREPARATION 12

7-(4-BROMOBUTYL)-4-METHYL-2,3-DIHYDRO-3-OXOBENZOXAZINE

Using the procedure described in Preparation 2, but replacing 6-(bromoacetyl)benzothiazolinone by 7-(4-bromobutyryl)-4-methyl-2,3-dihydro-3-oxobenzoxazine, described in Application EP 0,223,674, the product of the title is obtained.

PREPARATION 13

6-(4-BROMOBUTYL)BENZOXAZOLINONE

Using the procedure described in Preparation 2, but replacing 6-(bromoacetyl)benzothiazolinone by 6-(4-bromobutyryl)benzoxazolinone, described in Patent Application EP 0,281,309, the product of the title is obtained.

PREPARATION 14

3-METHYL-6-(4-BROMOBUTYL)BENZOXAZOLINONE

Using the procedure described in Preparation 13, but replacing 6-(4-bromobutyryl)benzoxazolinone by 3-methyl-6-(4-bromobutyryl)benzoxazolinone, the product of the title is obtained.

EXAMPLE 1

3-METHYL-6-(2-AMINOETHYL)BENZOTHIAZOLINONE (HYDROCHLORIDE)

In a 250 cm³ ground-necked flask, 8.1 g (0.03 mol) of 3-methyl-6-(2-bromoethyl)benzothiazolinone and 0.9 g of potassium iodide are dissolved in 120 cm³ of methanol and 30 cm³ of chloroform. A stream of gaseous ammonia is bubbled into the solution to the point of saturation, equivalent to approximately 2.6 g of ammonia, and a reflux condenser is then fitted. The temperature is stabilized at 50° C. with an oil bath and the mixture is left stirring magnetically for 72 hours. After cooling, the reaction mixture is evaporated on a water bath under vacuum. The residue is ground with distilled water acidified with 5% HCl solution, and then drained. The filtrate is recovered, washed with ethyl acetate and then alkalinized with 10% sodium hydroxide solution. It is extracted with chloroform, leaving the 2 phases agitating for ½ hour, and the organic phase is washed with distilled water and then dried over calcium chloride. The organic phase is evaporated on a water bath under vacuum, the residue is then taken up in absolute ethanol, a stream of gaseous HCl is bubbled through and the mixture is then evaporated to dryness on a water bath under vacuum. The product is dried and then recrystallized in absolute ethanol.

Yield: 32%
Melting point: 228°-230° C.
Molecular weight: 244.75 g/mol
Percentage composition:
Calculated : C 49.07; H 5.35; N 11.4;
Found : C 49.17; H 5.38; N 11.48;
Infrared spectrometry:
3100–2800 cm$^{-1}$ : ν (C-H)
2750–2400 cm$^{-1}$ : ν (NH+)
1680 cm$^{-1}$: ν (C=O) —O—CO—NR—
1600–1580 cm$^{-1}$ : ν (C=C) aromatic
Nuclear magnetic resonance spectrometry: Solvent: DMSO-d$_6$
δ = 3.00 ppm unresolved peaks; (4H)
δ = 3.38 ppm singlet; (3H) NCH$_3$
δ = 7.28 ppm unresolved peaks; (2H) H4,5 aromatic
δ = 7.55 ppm unresolved peaks; (1H) H7 aromatic
δ = 8.17 ppm signal; (3H) (NH3+)

The base is obtained by dissolution of the hydrochloride in water, alkalinization and three extractions with chloroform. The chloroform phases are combined, dried over calcium chloride and evaporated to dryness. The residue may be used without further purification as a starting material.

EXAMPLE 2

3-METHYL-6-2-N-(4-PHTHALIMIDOBUTYL)AMINOETHYL)BENZOTHIAZOLINONE

In a round-bottomed flask, 2.2 mmol of 3-methyl-6-(2-aminoethyl)benzothiazolinone, obtained in the previous example, are dissolved in 20 ml of dimethyl-formamide in the presence of 2.4 mmol of N-(4-bromobutyl)phthalimide, 6.6 mmol of potassium carbonate and a catalytic amount of potassium iodide. The mixture is left stirring at 60° C. for 6 hours. After cooling, the solvent is evaporated off and/or extracted with chloroform after adding water.

After washing, drying and evaporation of the organic phase, the expected product is obtained after purification by chromatography on a silica column, followed by crystallization.

$^1$H Nuclear Magnetic Resonance: Solvent: DMSO-d$_6$
δ = 1.75 ppm N—(CH$_2$)$_2$—CH$_2$—CH$_2$—phthalimido 2H, multiplet
δ = 3.38 ppm 3H, CH$_3$ singlet; (3H) NCH$_3$
δ = 3.62 ppm N—(CH$_2$)$_3$—CH$_2$—phthalimido 2H, triplet
Infrared:
3100–2800 cm$^{-1}$ : ν CH
1680 cm$^{-1}$ : ν CO (SCON)

EXAMPLE 3

3-METHYL-6-{2-[N-(4-PHTHALIMIDOBUTYL)-N-n-PROPYLAMINO]ETHYL} BENZOTHIAZOLINONE 1.5 mmol of 3-methyl-6-{2-[N-(4-phthalimido butyl)amino]ethyl}benzothiazolinone, obtained in Example 2, is dissolved in 15 ml of dimethylformamide in the presence of 4.4 mmol of 1-iodopropane and 4.4 mmol of potassium carbonate. After 24 hours' stirring at 60° C., the solvent is evaporated off and the reaction medium is taken up with 10 ml of water and extracted with chloroform. The organic phase is dried and evaporated and the expected product is obtained after purification by chromatography on a silica column, followed by crystallization.

$^1$H Nuclear Magnetic Resonance: Solvent: DMSO-d$_6$
δ = 0.88 ppm N—(CH$_2$)$_2$—CH$_3$; triplet (3H)
δ = 1.75 ppm N—(CH$_2$)$_2$—CH$_2$—CH$_2$-phthalimido; (2H), multiplet
δ = 3.38 ppm (3H), N—CH$_3$, singlet
δ = 3.62 ppm N—(CH$_2$)$_3$—CH$_2$—phthalimido (2H), triplet
Infrared:
3100–2800 cm$^{-1}$ : ν CH
1680 cm$^{-1}$ : ν CO (SCON)

EXAMPLE 4

-METHYL-6-(2-N-(3-PHTHALIMIDOPROPYL) AMINOETHYL)BENZOTHIAZOLINONE

Using the procedure described in Example 2, but replacing N-(4-bromobutyl)phthalimide by N-(3-bromopropyl)phthalimide, the product of the title is obtained.

$^1$H Nuclear Magnetic Resonance: Solvent: DMSO-$d_6$ $\delta = 3.38$ ppm, 3H, $CH_3$, singlet, N—$CH_3$
$\delta = 3.78$ ppm, 2H, $N(CH_2)_2$—$CH_2$—phthalimido
Infrared
3100–2800 $cm^{-1}$: v CH
1680 $cm^{-1}$: v CO (SCON)

EXAMPLE 5

3-METHYL-6-{2-N-(3-PHTHALIMIDOPROPYL)-N-n-PROPYLAMINO ETHYL} BENZOTHIAZOLINONE

Using the procedure described in Example 3, but replacing 3-methyl-6-{2[N-(4-phthalimidobutyl)amino]-ethyl} benzothiazolinone by 3-methyl-6-{2-[N-(3-phthalimidopropyl) amino]ethyl}benzothiazolinone, obtained in Example 4, the expected product is obtained.

$^1$H Nuclear Magnetic Resonance: Solvent: DMSO-d6

$\delta = 0.89$ ppm, 3H, N—$CH_2$—$CH_2$—$CH_3$, triplet
$\delta = 3.38$ ppm, 3H, N—$CH_3$, singlet
Infrared
3100–2800 $cm^{-1}$: v CH
1680 $cm^{-1}$: v CO (SCON)

EXAMPLE 6

3-METHYL-6-{2-[N-(2-PHTHALIMIDOETHYL)AMINO] ETHYL}BENZOTHIAZOLINONE

Using the procedure described in Example 2, but replacing N-(4-bromobutyl)phthalimide by N-(2-bromoethyl)phthalimide and leaving the reactants stirring for 40 hours, the expected product is obtained.

$^1$H Nuclear Magnetic Resonance: Solvent: DMSO-$d_6$ $\delta = 3.39$ ppm, 3H, $CH_3$, singlet, N—$CH_3$
$\delta = 3.80$ ppm, 2H, $N(CH_2)_2$—$CH_2$—phthalimido
Infrared
3100–2800 $cm^{-1}$: v CH
1680 $cm^{-1}$: v CO (SCON)

EXAMPLE 7:

3-METHYL-6-{2-[N-(2-PHTHALIMIDOETHYL)-N-n-PROPYLAMINO]-ETHYL} BENZOTHIAZOLINONE

Using the procedure described in Example 3, but replacing 3-methyl-6-{2-[N-(4-phthalimidobutyl)amino]-ethyl} benzothiazolinone by 3-methyl-6-{2-[N-(2-phthalimidoethyl) amino]ethyl}benzothiazolinone, the product of the title is obtained.

$^1$H Nuclear Magnetic Resonance: Solvent: DMSO-$d_6$ $\delta = 3.39$ ppm, 3H, $CH_3$, singlet, N—$CH_3$
Infrared:
3100–2800 $cm^{-1}$: v CH
1680 $cm^{-1}$: v CO (SCON)

EXAMPLE 8:

3-[4-{N-[2-(3-METHYLBENZOTHIAZOLINON-6-YL)ETHYL]AMINO}BUTYL]-2,4-DIOXO-3-AZASPIRO [4.5]DECANE

Using the procedure described in Example 2, but replacing N-(4-bromobutyl)phthalimide by N-(4-bromo-butyl)2,4-dioxo-3-azaspiro[4.5]decane and leaving the reactants stirring for 24 hours, the product of the title is obtained.

$^1$H Nuclear Magnetic Resonance: Solvent: DMSO-$d_6$ $\delta = 2.59$ ppm, 4H, singlet, $N(CO$—$CH_2)_2$
$\delta = 3.50$ ppm, 3H, singlet, N—$CH_3$
Infrared:
3000–2800 $cm^{-1}$: v CH
1600–1680 $cm^{-1}$: v CO (overlapping)

EXAMPLE 9

3-[4-{N-[2-(3-METHYLBENZOTHIAZOLINON-6-YL)ETHYL]-N-PROPYL AMINO}BUTYL]-2,4-DIOXO-3-AZASPIRO[4.5]-DECANE

Using the procedure described in Example 3, but replacing the compound obtained in Example 2 by the compound obtained in Example 8, the product of the title is obtained.

EXAMPLE 10

3-[4-{N-[2-(3-METHYLBENZOTHIAZOLINON-6-YL)ETHYL]AMINO}BUTYL]-2,4-DIOXO-3-AZABICYCLO[3.3.0]OCTANE

Using the procedure described in Example 2, but replacing N-(4-bromobutyl)phthalimide by N-(4-bromobutyl)-2,4-dioxo-3-azabicyclo [3.3.0]octane and leaving the reactants stirring for 24 hours, the product of the title is obtained.

$^1$H Nuclear Magnetic Resonance: Solvent: DMSO-$d_6$ $\delta = 3.39$ ppm, 3H, N—$CH_3$,
$\delta = 3.49$ ppm, 2H, triplet, $CH_2$—N (azabicyclooctane)
Infrared:
3100–2800 $cm^{-1}$ v CH
1680 $cm^{-1}$: v CO (SCON)

EXAMPLE 11

3-METHYL-6-[2-{N-[4-(4,4-DIMETHYL-2,6-DIOXO-1-PIPERIDYL) BUTYL] AMINO}ETHYL]BENZOTHIAZOLINONE

Using the procedure described in Example 2, but replacing N-(4-bromobutyl)phthalimide by N-(4-bromobutyl)-4,4-dimethyl-2,6-dioxopiperidine and leaving the reactants stirring for 24 hours, the expected product is obtained.

$^1$H Nuclear Magnetic Resonance: Solvent: DMSO-$d_6$ $\delta = 1.06$ ppm, 6H, singlet $C(CH_3)_2$
$\delta = 3.39$ ppm, N—$CH_3$ 3H, singlet
Infrared:
1680 $cm^{-1}$: v CO (SCON)

EXAMPLE 12

3-METHYL-6-[2-{N-[4-(4,4-DIMETHYL-2-OXO-1-PIPERIDYL)BUTYL] AMINO} ETHYL BENZOTHIAZOLINONE

Using the procedure described in Example 2, but replacing N-(4-bromobutyl)phthalimide by 1-(4-bromobutyl)4,4-dimethyl-2-oxopiperidine and leaving the reactants stirring for 24 hours, the expected product is obtained.

EXAMPLE 13

3-METHYL-6-[2-{N-[4-(2-OXO-1-PIPERIDYL)-BUTYL]AMINO}-ETHYL] BENZOTHIAZOLINONE

Using the procedure described in Example 2, but replacing N-(4-bromobutylphthalimide) by 1-(4-bromobutyl)-2-oxopiperidine and leaving the reactants stirring for 24 hours, the expected product is obtained.

EXAMPLE 14

3-METHYL-6-[2-(N-METHYL-N-BENZYLAMINO)ETHYL]BENZOTHIAZOLINONE 0.04 mol of N-methyl-N-benzylamine and 0.02 mol of 3-methyl-6-(2-bromoethyl)benzothiazolinone, the latter being dissolved beforehand in 120 cm$^3$ of dioxane, are introduced into a 100-cm3 ground-necked flask fitted with a reflux condenser. The mixture is heated to reflux for 96 hours with magnetic stirring. After cooling, the reaction mixture is filtered and the filtrate is then evaporated on a water bath under vacuum. The residue is taken up with 50 cm$^3$ and alkalinized with 10 cm3 of normal sodium hydroxide solution.

The mixture is extracted three times with 60 cm$^3$ of chloroform. The organic solutions are combined, dried over calcium chloride, filtered and evaporated on a water bath under vacuum. The residue is taken up with petroleum ether, drained, dried and recrystallized.

$^1$H Nuclear Magnetic Resonance: Solvent: DMSO-d$_6$

δ = 2.22 ppm, N—CH$_3$(CH$_2$—N—CH$_3$), singlet 3H

δ = 3.37 ppm, N—CH$_3$ (benzothiazolinone), singlet 3H

δ = 3.53 ppm, N—CH$_2$—C$_6$H$_5$, 2H, singlet

EXAMPLE 15

3-METHYL-6-[2-(N-METHYLAMINO)ETHYL]-BENZOTHIAZOLINONE (HYDROCHLORIDE)

Using the procedure described in Example 1, but replacing ammonia by N-methylamine, the product of the title is obtained.

$^1$H Nuclear Magnetic Resonance: Solvent D$_2$O (hydrochloride)

δ = 2.84 ppm, singlet 3H, N—CH$_3$

δ = 3.29 ppm, singlet 3H, N—CH$_3$

Infrared:

3100–2600 cm$^{-1}$ : ν NH and νCH 1680 cm$^{-1}$ : ν CO (SCON)

EXAMPLE 16

3-METHYL-6-(2-PROPYLAMINOETHYL)BENZOTHIAZOLINONE HYDROCHLORIDE

Using the procedure described in Example 16, but replacing isopropylamine by n-propylamine, the product of the title is obtained.

Spectral characteristics:

Infrared:

3100–2650 cm$^{-1}$ : ν NH and ν CH 1680 cm$^{-1}$ : ν CO (SCON)

EXAMPLE 17

3-METHYL-6-[2-(N-METHYL-N-CYANOMETHYLAMINO)ETHYL] BENZOTHIAZOLINONE

In a round-bottomed flask, 6.8 mmol of 3-methyl-6-[2-(N-methylamino)ethyl]benzothiazolinone are dissolved in 50 mol of dioxane in the presence of 20 mmol of chloro-acetonitrile, 20 mmol of potassium carbonate and a catalytic amount of potassium iodide. The mixture is stirred at 60° C. for 48 hours. After cooling, the solvent is evaporated off and the reaction mixture is extracted with chloroform after adding water. After washing, drying and evaporation of the organic phase, the expected product is obtained after purification by chromatography on a silica column, followed by crystallization.

$^1$H Nuclear Magnetic Resonance, DMSO-d$_6$

δ = 3.39 ppm, singlet, 3H, N—CH$_3$

Infrared:

1680 cm$^{-1}$ : ν CO (SCON)

EXAMPLE 18

3-METHYL-6-{2-[N-METHYL-N-(2-AMINOETHYL AMINO]ETHYL} BENZOTHIAZOLINONE

In a ground-necked flask, 6 mmol of 3-methyl-6-[2-(N-methylamino)ethyl]benzothiazolinone are dissolved in 50 ml of dioxane, 20 mmol of 1-chloro-2-bromoethane and 20 mmol of potassium carbonate. The mixture is stirred for 48 hours at a temperature of 60° C. After cooling, the mixture is evaporated and the reaction medium is extracted with chloroform after adding water. After washing, drying and evaporation of the organic phase, 3-methyl-6-{2-[N-methyl-N-(2-chloroethyl) amino]ethyl}benzothiazolinone is obtained, which product is transferred to a ground-necked flask. A catalytic amount of potassium iodide, 25 cm$^3$ of methanol and 10 cm$^3$ of chloroform are added. A stream of gaseous ammonia is bubbled into the solution to the point of saturation and a reflux condenser is then fitted. The temperature is stabilized at 50° C. with an oil bath and the mixture is then left stirring magnetically for 72 hours. After cooling, the reaction mixture is evaporated on a water bath under vacuum. The residue is ground with distilled water acidified with 5% HCl solution, and then drained. The filtrate is recovered, washed with ethyl acetate and then alkalinized with 10% sodium hydroxide solution. It is extracted with chloroform, leaving the 2 phases agitating for ¼ hour, and the organic phase is washed with distilled water and then dried over calcium chloride. The organic phase is evaporated on a water bath under vacuum, the residue is then taken up in absolute ethanol, a stream of gaseous HCl is bubbled through and the mixture is then evaporated to dryness on a water bath under vacuum. The product is dried and then recrystallized.

$^1$H Nuclear Magnetic Resonance:

δ = 3.38 ppm, singlet, 3H, N—CH$_3$

Infrared:

1680 cm$^{-1}$ : ν CO (SCON)

EXAMPLE 19

3-METHYL-6-[2-{N-METHYL-N-[2-(PARA TOLYLSULFONYLAMINO) ETHYL] AMINO} ETHYL] BENZOTHIAZOLINONE 4 mmol of 3-methyl-6-{2-[N-methyl-N-(2-aminoethyl)amino]ethyl}benzothiazolinone, obtained in Example 19, are dissolved in 50 ml of dichloromethane cooled in ice, and 11.4 mmol of triethylamine are added dropwise, followed by 4 mmol of tosyl chloride dissolved in dichloromethane.

The mixture is left stirring for 30 minutes at room temperature. The solvent is then evaporated off and the expected product is obtained after purification by chromatography on a silica column.

Nuclear Magnetic Resonance: 1H (CDCl$_3$)
$\delta = 3.39$ ppm, singlet, 3H, N—C$\underline{H}_3$
Infrared:
1680 cm$^{-1}$: v CO (SCON)

EXAMPLE 20

3-METHYL-6-[2-(N-PROPYL-N-CYANOMETHYLAMINO)ETHYL] BENZOTHIAZOLINONE

Using the procedure described in Example 18, but replacing 3-methyl-6-[2-(N-methylamino)ethyl]benzothiazolinone by 3-methyl-6-[2-(N-propylamino)ethyl]-benzothiazolinone, the product of the title is obtained.

Nuclear Magnetic Resonance 1H (CDCl$_3$)
$\delta = 3.39$ ppm, singlet, 3H, N—C$\underline{H}_3$
Infrared:
680 cm$^{-1}$: v CO (SCON)

EXAMPLE 21

3-METHYL-6-{2-[N-PROPYL-N-(2-AMINOETHYL)AMINO]ETHYL} BENZOTHIAZOLINONE

Using the procedure described in Example 19, but replacing 3-methyl-6-[2-(N-methyl-N-cyanomethylamino)-ethyl] benzothiazolinone by 3-methyl-6-[2-(N-propyl-N-cyanomethylamino)ethyl]benzothiazolinone, the product of the title is obtained.

EXAMPLE 22

3-METHYL-6-[2-{N-PROPYL-N-[2-(PARA-TOLYLSULFONYLAMINO)ETHYL] AMINO} ETHYL]BENZOTHIAZOLINONE

Using the procedure described in Example 20, but replacing 3-methyl-6-{2-[N-methyl-N-(2-aminoethyl)amino] ethyl} benzothiazolinone by 3-methyl-6-{2-[N-propyl-N-(2-aminoethyl)amino]ethyl}benzothiazolinone, the product of the title is obtained

EXAMPLE 23

3-METHYL-6-[2-{(N-PROPYL-N-[3-PARA-TOLYLSULFONYLAMINO)-PROPYL] AMINO} ETHYL] BENZOTHIAZOLINONE

Using the procedure described in Example 19, but replacing 1-chloro-2-bromoethane by 1-chloro-3-bromopropane and 3-methyl-6-[2-(N-methylamino)ethyl]benzothiazolinone by 3-methyl-6-[2-(N-n-propylamino) ethyl]-benzothiazolinone, 3-methyl-6-{2-[N-methyl-N-(3-aminopropyl)amino]ethyl} benzothiazolinone is obtained, which product is treated as in Example 20 with tosyl chloride to yield the product of the title.

Nuclear Magnetic Resonance: 1H (CDCl$_3$)

$\delta = 3.38$ ppm, singlet, 3H, N—C$\underline{H}_3$

Infrared 1760 cm$^{-1}$: v CO (SCON)

EXAMPLE 24

3-METHYL-6-[2-{N-PROPYL-N-[4-(PARA-TOLYLSULFONYLAMINO)-BUTYL] AMINO}ETHYL]BENZOTHIAZOLINONE

Using the procedure described in Example 24, but replacing 1-chloro-3-bromopropane by 1-chloro-bromobutane, the product of the title is obtained.

EXAMPLE 25

3-METHYL-6-(4-AMINOBUTYL)BENZOTHIAZOLINONE (HYDROCHORIDE)

Using the procedure described in Example 1, but replacing 3-methyl-6-(2-bromoethyl)benzothiazolinone by 3-methyl-6-(4-chlorobutyl)benzothiazolinone, 3-methyl-6-(4-aminobutyl)benzothiazolinone (hydrochloride) is obtained.

EXAMPLES 26 TO 37

Using the procedure described in Examples 2 to 13, but replacing 3-methyl-6-(2-aminoethyl)benzothiazolinone by 3-methyl-6-(4-aminobutyl)benzothiazolinone of Example 33, the following are obtained:

EXAMPLE 26

3-METHYL-6-{4-[N-(4-PHTHALIMIDOBUTYL)AMINO]BUTYL} BENZOTHIAZOLINONE

EXAMPLE 27

3-METHYL-6-{4-[N-(4-PHTHALIMIDOBUTYL)-N-n-PROPYLAMINO]-BUTYL}BENZO-THIAZOLINONE

EXAMPLE 28

3-METHYL-6-{4-[N-(3-PHTHALIMIDOPROPYL-)AMINO]BUTYL}-BENZOTHIAZOLINONE

EXAMPLE 29

3-METHYL-6-{4-[N-(3-PHTHALIMIDOPROPYL)-N-PROPYLAMINO]BUTYL)}BENZOTHIAZOLINONE

EXAMPLE 30

3-METHYL-6-{4-[N-(2-PHTHALIMIDOETHYL)-N-n-PROPYLAMINO]BUTYL}BENZO-THIAZOLINONE

EXAMPLE 31

3-METHYL-6-{4-[N-(2-PHTHALIMIDOETHYL)AMINO]BUTYL}BENZOTHIAZOLINONE

EXAMPLE 32

3-[4-{N-[4-(3-METHYLBENZOTHIAZOLINON-6-YL)BUTYL]AMINO}-BUTYL]2,4-DIOXO-3-AZASPIRO[4.5]DECANE

EXAMPLE 33

3-[4-{N-[4-(3-METHYLBENZOTHIAZOLINON-6-YL)BUTYL]-N-n-PROPYL AMINO}BUTYL]-2,4-DIOXO-3-AZASPIRO[4.51]-DECANE

EXAMPLE 34

3-[4-{N-[4-(3-METHYLBENZOTHIAZOLINON-6-YL)BUTYL]AMINO}-BUTYL]-2,4-DIOXO-3-AZABICYCLO[3.3.0.]OCTANE

EXAMPLE 35

3-METHYL-6-[4-{N-[4-(4,4-DIMETHYL-2,6 DIOXO-1-PIPERIDYL)-BUTYL] AMINO}BUTYL]BENZOTHIAZOLINONE

EXAMPLE 36

3-METHYL-6-[4-{N-[4-(4,4-DIMETHYL-2-OXO-1-PIPERIDYL) BUTYL] AMINO}BUTYL]BENZOTHIAZOLINONE

EXAMPLE 37

3-METHYL-6-[4-{N-[4-(2-OXO-1-PIPERIDYL) BUTYL]AMINO} BUTYL] BENZOTHIAZOLINONE

EXAMPLE 38

3-METHYL-6-[4-(N-METHYL-N-BENZYLAMINO)BUTYL] BENZOTHIAZOLINONE

Using the procedure described in Example 14, but replacing 3-methyl-6-(2-bromoethyl)benzothiazolinone by 3-methyl-6-(4-bromobutyl)benzothiazolinone, the product of the title is obtained.

EXAMPLE 39

3-METHYL-6-[4-(N-METHYLAMINO)BUTYL]-BENZOTHIAZOLINONE

Using the procedure described in Example 15, but replacing 3-methyl-6-[2-(N-methyl-N-benzylamino)ethyl]benzothiazolinone by 3-methyl-6-4-(N-methyl-N-benzylamino)butylbenzothiazolinone, obtained in the previous example, the product of the title is obtained.

EXAMPLES 40 TO 42

Using the procedure described in Examples 18 to 20, but repalcing 3-methyl-6-[2-(N-methylamino)ethyl]benzothiazolinone by 3-methyl-6-[4-(N-methylamino)-butylbenzothiazolinone, the following are obtained:

EXAMPLE 40

3-METHYL-6 -[4-N-METHYL-N-CYANOMETHYLAMINO)-BUTYL]BENZOTHIAZOLINONE

EXAMPLE 41

3-METHYL-6-{4-[N-METHYL-N-(2-AMINOETHYL)AMINO]-BUTYL}BENZOTHIAZOLINONE

EXAMPLE 42

3-METHYL-6-[4-{N-METHYL-N-2-(PARA-TOLYLSULFONYLAMINO)ETHYL]AMINO} BUTYL]BENZOTHIAZOLINONE

EXAMPLE 43

7-{2-[N-(4-PHTHALIMIDOBUTYL)AMINO]ETHYL}BENZOTHIAZOLINONE

Using the procedure described in Example 2, but replacing 3-methyl-6-(2-aminoethyl)benzothiazolinone by 7-(2-aminoethyl)benzothiazolinone, described in Example 8 of European Patent Application 174,811, the product of the title is obtained.

Using the same procedure as in Examples 3 to 13, but employing 7-(2-aminoethyl)benzothiazolinone as a starting material, the following are obtained:

EXAMPLE 44

7-{2-[N-(4-PHTHALIMIDOBUTYL)-N-n-PROPYLAMINO]ETHYL}BENZOTHIAZOLINONE

EXAMPLE 45

7-{2-[N-(3-PHTHALIMIDOPROPYL)AMINO]ETHYL}-BENZOTHIAZOLINONE

EXAMPLE 46

7-{2-[N-(3-PHTHALIMIDOPROPYL)-N-n-PROPYLAMINO] ETHYL} BENZOTHIAZOLINONE

EXAMPLE 47

7-{2-[N-(2-PHTHALIMIDOETHYL)AMINO]ETHYL}BENZOTHIAZOLINONE

EXAMPLE 48

7-{2-[N-(2-PHTHALIMIDOETHYL)-N-n-PROPYLAMINO]ETHYL}-BENZOTHIAZOLINONE

EXAMPLE 49

3-[4-{N-[2-(BENZOTHIAZOLINON-7-YL)ETHYL]AMINO}BUTYL]-2,4-DIOXO-3-AZASPIRO[4.5]-DECANE

EXAMPLE 50

3-[4-{(N-[2-(BENZOTHIAZOLINON-7-YL)ETHYL]-N-n-PROPYL-AMINO}BUTYL]2,4-DIOXO-3-AZASPIRO[4.5]DECANE

EXAMPLE 51

3-[4-{N-[2-(BENZOTHIAZOLINON-7-YL)ETHYL]AMINO}BUTYL]-2,4-DIOXO-3AZABICYCLO[3.3.0]OCTANE

EXAMPLE 52

7-[2-{N-[4-(4,4-DIMETHYL-2,6-DIOXO-1-PIPERIDYL)BUTYL]AMINO}ETHYL]BENZOTHIAZOLINONE

EXAMPLE 53

7-[2-{N-[4-(4,4-DIMETHYL-2-OXO-1-PIPERIDYL)-BUTYL]AMINO}ETHYL]BENZOTHIAZOLINONE

EXAMPLE 54

7-[2-{N-[4-(2-OXO-1-PIPERIDYL)BUTYL]AMINO}ETHYL]BENZOTHIAZOLINONE

EXAMPLE 55

4 ETHYL-7-(4-AMINOBUTYL)-2,3-DIHYDRO-3-OXO-1,4-BENZOXAZINE

Employing 4-methyl-7-(4-bromobutyl)-2,3-dihydro-3-oxobenzoxazine in Example 1 instead of 3-methyl-6-(2-bromoethyl)benzothiazolinone, the product of the title is obtained.

EXAMPLES 56 TO 67

Using the procedure described in Examples 2 to 13, but employing 7-(4-aminobutyl)-4-methyl-2,3-dihydro-3-oxobenzoxazine instead of 3-methyl-6-(2-bromoethyl)benzothiazolinone, the following are obtained:

EXAMPLE 56

4-METHYL-7-{4-[N-(4-PHTHALIMIDOBUTYL)AMINO]BUTYL}-2,3-DIHYDRO-3-OXO-1,4-BENZOXAZINE

EXAMPLE 57

4-METHYL-7-{4-[N-(4-PHTHALIMIDOBUTYL)-N-n-PROPYLAMINO]BUTYL}-2,3-DIHYDRO-3-OXO-1,4 -BENZOXAZINE

EXAMPLE 58

4-METHYL-7-(4-[N-(3-PHTHALIMIDOPROPYL)AMINO]BUTYL}-2,3-DIHYDRO -3-OXO-1,4-BENZOXAZINE

EXAMPLE 59

4-METHYL-7-{4-[N-(3-PHTHALIMIDOPROPYL)-N-n-PROPYLAMINO]-BUTYL}2,3-DIHYDRO-3-OXO-1,4-BENZOXAZINE

EXAMPLE 60

4-METHYL-7-{4-[N-(2-PHTHALIMIDOETHYL)AMINO]BUTYL}-2,3-DIHYDRO-3-OXO-1,4-BENZOXAZINE

EXAMPLE 61

4-METHYL-7-{4-[N-(2-PHTHALIMIDOETHYL)-N-n-PROPYLAMINO]BUTYL}2,3-DIHYDRO-3-OXO-1,4-BENZOXAZINE

EXAMPLE 62

3-[4-{N-[4-(4-METHYL-2,3-DIHYDRO 3-OXO 1,4-BENZOXAZIN-7-YL) BUTYL]AMINO}BUTYL]-2.4-DIOXO-3-AZASPIRO[4.51]DECANE

EXAMPLE 63

3-[4-{N-[4-(4-METHYL-2,3-DIHYDRO-3-OXO-1,4-BENZOXAZIN-7-YL) BUTYL]-N-n-PROPYLAMINO}BUTYL]-2,4-DIOXO-3-AZASPIRO-[4.5]DECANE

EXAMPLE 64

3-[4-{N-4-(4-METHYL-2,3-DIHYDRO-3-OXO-1,4-BENZOXAZIN-7-YL) BUTYL]AMINO}BUTYL]-2,4-DIOXO-3-AZABICYCLO[3.3.0]-OCTANE

EXAMPLE 65

4-METHYL-7-[4-{N-[4-(4,4-DIMETHYL-2,6-DIOXO-1-PIPERIDYL)BUTYL] AMINO}BUTYL]-2,3-DIHYDRO-3-OXO-1,4-BENZOXAZINE

EXAMPLE 66

4-METHYL-7-[4-{N-[4-(4,4-DIMETHYL-2-OXO-1-PIPERIDYL)BUTYL] AMINO}BUTYL]-2,3-DIHYDRO-3-OXO-1,4-BENZOXAZINE

EXAMPLE 67

4-METHYL-7-[4-{N-[4-2-OXO-1-PIPERIDYL)BUTYL]AMINO}-BUTYL]-2,3 -DIHYDRO-3-OXO-1,4-BENZOXANINE

EXAMPLES 68 TO 71

Employing as in Examples 14 to 17 4-methyl-7-(4-bromobutyl)-2,3-dihydro-3-oxo-1,4-benzoxazine as a starting material instead of 3-methyl-6-(2-bromoethyl)-benzothiazolinone, the following is obtained:

EXAMPLE 68

4-METHYL-7-[4-(N-METHYL-N-BENZYLAMINO)BUTYL]-2,3-DIHYDRO-3-OXO1,4-BENZOXAZINE which on catalytic hydrogenation yields:

EXAMPLE 69

4-METHYL-7-[4-(N-METHYLAMINO)BUTYL]-2,3-DIHYDRO-3-OXO-1,4-BENZOXAZINE

EXAMPLE 70

4-METHYL-7-[4-(ISOPROPYLAMINOBUTYL)-2,3-DIHYDRO-3-OXO-1,4-BENZOXAZINE

EXAMPLE 71

4-METHYL-7-[4-n-PROPYLAMINOBUTYL -2,3-DIHYDRO-3-OXO-1,4-BENZOXAZINE

EXAMPLE 72

4-METHYL-7-[4-(N-METHYL-N-CYANOMETHYLAMINO)BUTYL]-2,3-DIHYDRO-3-OXO-1,4-BENZOXAZINE

Using the procedure described in Example 18, but replacing 3-methyl-6-2-(N-methylamino)ethylbenzothiazolinone by 4-methyl-7-4-(N-methylamino)butyl-2,3-dihydro-3-oxo-1,4-benzoxazine, the product of the title is obtained.

Using the procedure described in Examples 19 and 20 with the product of Example 72, the following are obtained:

EXAMPLE 73

4-METHYL-7-{4-[N-METHYL-N-(2-AMINOETHYL)AMINO]BUTYL}-2,3-DIHYDRO-3-OXO-1,4-BENZOXAZINE

EXAMPLE 74

4-METHYL-7-[4-{N-METHYL-N-[2-(PARA-TOLYLSULFONYLAMINO) ETHYL] AMINO}BUTYL]-2,3-DIHYDRO-3-OXO-1,4-BENZOXAZINE

EXAMPLE 75

4-METHYL-7-[4-{N-n-PROPYL-N-[3-PARA-TOLYLSULFONYLAMINO) PROPYL]AMINO}BUTYL]-2,3-DIHYDRO-3-OXO-1,4-BENZOXAZINE

Using the procedure described in Example 24, but i5 replacing 3-methyl-6-(2-propylaminoethyl)benzothiazolinone by 4-methyl-7-(4-propylaminobutyl)-2,3-dihydro-3-oxo-1,4benzoxazine, the product of the title is obtained.

EXAMPLE 76

4-METHYL-7-[4-{N-n-PROPYL-N-[4-(PARA-TOLYLSULFONYLAMINO)BUTYL] AMINO}BUTYL]-2,3-DIHYDRO-3-OXO-1,4-BENZOXAZINE

Using the procedure described in Example 75, but replacing 1-chloro-3-bromopropane by 1-chloro-4-bromobutane, the product of the title is obtained.

EXAMPLE 77

7-(2-AMINOETHYL)-3-OXO-2,3-DIHYDRO-1,4-BENZOXAZINE

In a 250-cm$^3$ ground-necked flask, 0.01 mol of 7-(2-bromoethyl)-3-oxo-2,3-dihydro-1,4-benzoxazine and 0.3 g of potassium iodide are dissolved in 30 cm$^3$ of dimethylformamide.

A stream of gaseous ammonia is bubbled into the solution to the point of saturation and a reflux condenser is fitted. The temperature is stabilized at 50° C. with an oil bath and the mixture is then left stirring magnetically for 72 hours. After cooling, the reaction mixture is evaporated on a water bath under vacuum. The residue is ground in distilled water acidified with 5% HCl solution, and then drained. The filtrate is recovered, washed with ethyl acetate and then alkalinized with 10% sodium hydroxide solution. It is extracted with chloroform, leaving the 2 phases agitating for ½ hour, and the organic phase is washed with distilled water and then dried over calcium chloride. The organic phase is evaporated on a water bath under vacuum, the residue is then taken up in absolute ethanol, a stream of gaseous HCl is bubbled through and the mixture is then evaporated to dryness on a water bath under vacuum. The product is dried and then recrystallized.

EXAMPLE 78

4-METHYL-7-(2-PROPYLAMINOETHYL)-3-OXO-2,3-DIHYDRO-1,4BENZOXAZINE

Using the procedure described in Preparation 9, but replacing 6-(2-bromoethyl)-3-oxo-2,3-dihydro-1,4-benzoxazine by 4-methyl-7-(2-bromoethyl)-3-oxo-2,3-dihydro-1,4benzoxazine, the product of the title is obtained.

EXAMPLES 79 to 90

Using the procedure described in Examples 2 to 13, but employing 7-(2-aminoethyl)-4-methyl-3-oxo-2,3-dihydro-1,4benzoxazine instead of 3-methyl-6-(2-bromoethyl) benzothiazolinone, the following are obtained:

EXAMPLE 79
4-METHYL-7-{2-[N-(4-PHTHALIMIDOBUTYL)AMINO]ETHYL}-3-OXO-2,3-DIHYDRO-1,4-BENZOXAZINE

EXAMPLE 80
4-METHYL 7-{2-[N-(4-PHTHALIMIDOBUTYL-N-n-PROPYLAMINO]ETHYL}-3-OXO-2,3-DIHYDRO-1,4-BENZOXAZINE

EXAMPLE 81
4-METHYL-7-{2-[N-(3-PHTHALIMIDOPROPYL)AMINO]ETHYL}-3-OXO-2,3-DIHYDRO-1,4-BENZOXAZINE

EXAMPLE 82
4-METHYL-7-{2-[N-(3-PHTHALIMIDOPROPYL)-N-n-PROPYLAMINO]ETHYL}-3-OXO-2,3-DIHYDRO-1,4-BENZOXAZINE

EXAMPLE 83
4-METHYL-7-{2-[N-(2-PHTHALIMIDOETHYL)AMINO]ETHYL}-3-OXO-2,3-DIHYDRO-1,4-BENZOXAZINE

EXAMPLE 84
4-METHYL-7-{2-[N-(2-PHTHALIMIDOETHYL)-N-n-PROPYLAMINO]ETHYL}-3-oxo-2,3-DIHYDRO-1,4-BENZOXAZINE

EXAMPLE 85
3-[4-{N-[2-(4-METHYL-3-OXO-2,3-DIHYDRO-1,4-BENZOXAZIN-7-YL)ETHYL]AMINO}BUTYL]-2,4-DIOXO-3-AZASPIRO[4.5]DECANE

EXAMPLE 86
3-[4-{N-[2-(4-METHYL-3-OXO-2,3-DIHYDRO-1,4-BENZOXAZIN-7-YL)ETHYL]-N-n-PROPYLAMINO}BUTYL]-2,4-DIOXO-3-AZASPIRO[4.5]DECANE

EXAMPLE 87
3-[4-{N-[2-(4-METHYL-3-OXO-2,3-DIHYDRO-1,4-BENZOXAZIN-7-YL)ETHYL]AMINO}BUTYL]-2,4-DIOXO-3-AZABICYCLO[3.3.0]OCTANE

EXAMPLE 88
4-METHYL-7-[2-{N-[4-(4,4-DIMETHYL-2,6-DIOXO-1-PIPERIDYL)BUTYL]AMINO}ETHYL]-3-OXO-2,3-DIHYDRO-1.4-BENZOXAZINE

EXAMPLE 89
4-METHYL-7-[2-{N-[4-(4,4-DIMETHYL-2-OXO-1-PIPERIDYL)-BUTYL]AMINO}ETHYL]-3-OXO-2,3-DIHYDRO-1,4-BENZOXAZINE

EXAMPLE 90
4-METHYL-7-[2-{N-[4-(2-OXO-1-PIPERIDYL)-BUTYL]AMINO}ETHYL]-3-OXO-2,3-DIHYDRO-1,4-BENZOXAZINE

EXAMPLE 91
4-METHYL-7-[2-{N-PROPYL-N-CYANOMETHYLAMINO)ETHYL]-3-OXO-2,3-DIHYDRO-1,4-BENZOXAZINE

Using the procedure described in Example 18, but replacing 3-methyl-6-2-(N-methylamino)ethylbenzothiazolinone by 4-methyl-7-2-(N-propylamino)ethyl-3-oxo-2,3-dihydro-1,4benzoxazine, the product of the title is obtained.

Using the procedure described in Examples 19 and 20 with the product of Example 91, the following are obtained, respectively:

EXAMPLE 92
4-METHYL-7-{2-[N-PROPYL-N-(2-AMINOETHYL)AMINO]ETHYL}-3-oxo-2,3-DIHYDRO-1,4-BENZOXAZINE

EXAMPLE 93
4-METHYL-7-[2-{N-PROPYL-N-[2-(PARA-TOLYLSULFONYLAMINO)ETHYL]AMINO}ETHYL]-3 oxo-2,3-DIHYDRO-1,4-BENZOXAZINE

EXAMPLE 94
4-METHYL-7-[2-=N-PROPYL-N-[3-(PARA-TOLYLSULFONYLAMINO)-PROPYL] AMINO}ETHYL]-3-OXO-2,3-DIHYDRO-1,4-BENZOXAZINE

Using the procedure described in Example 24, but replacing 3-methyl-6-(2-propylaminoethyl)benzothiazolinone by 4-methyl-7-(2-propylaminoethyl -3-oxo-2,3-dihydro-1,4-benzoxazine, the product of the title is obtained.

EXAMPLE 95
4-METHYL-7-[2-{N-PROPYL-N-{4-(PARA-TOLYLSULFONYLAMINO)-BUTYL] AMINO}ETHYL]-3-oxo-2,3-DIHYDRO-1,4-BENZOXAZINE Using the procedure described in Example 94, but replacing 1-chloro-3-bromopropane by 1-chloro-4-bromobutane, the product of the title is obtained.

EXAMPLE 96
6-(2-AMINOETHYL)-3-OXO-2,3-DIHYDRO-1,4-BENZOXAZINE

In a 250-cm$^3$ ground-necked flask, 0.01 mol of 6-(2-bromoethyl)-3-oxo-2,3-dihydro-1,4-benzoxazine and 0.3 g of potassium iodide are dissolved in 30 cm$^3$ of dimethylformamide.

A stream of gaseous ammonia is bubbled into the i5 solution to the point of saturation and a reflux condenser is fitted. The temperature is stabilized at 50° C. with an oil bath and the mixture is then left stirring magnetically for 72 hours. After cooling, the reaction mixture is evaporated on a water bath under vacuum. The residue is ground with distilled water acidified with 5% HCl solution, and then drained. The filtrate is recovered, washed with ethyl acetate and then alkalinized with 10% sodium hydroxide solution. It is extracted with chloroform, leaving the 2 phases agitating for ½ hour, and the organic phase is washed with distilled water and then dried over calcium chloride. The organic phase is evaporated on a water bath under vacuum, the residue is then taken up in absolute ethanol, a stream of gaseous HCl is passed through and the mixture is then evaporated to dryness on a water bath under vacuum. The product is dried and then recrystallized.

EXAMPLES 97 TO 109

Using the procedure described in Examples 2 to 13, but employing 6-(2-aminoethyl)-3-oxo-2,3-dihydro-1,4- benzoxazine instead of 3-methyl-6-(2-bromoethyl)benzothiazolinone, the following are obtained:

EXAMPLE 97
6-{2-[N-(4-PHTHALIMIDOBUTYL)AMINO]ETHYL}-3-OXO-2,3-DIHYDRO-1,4BENZOXAZINE

EXAMPLE 98
6-{2-[N-(4-PHTHALIMIDOBUTYL)-N-n-PROPYLAMINO]ETHYL}-3-OXO-2,3-DIHYDRO-1,4-BENZOXAZINE

EXAMPLE 99
6-{2-[N-(3-PHTHALIMIDOPROPYL)AMINO]ETHYL}-3-OXO-2,3-DIHYDRO-1,4BENZOXAZINE

EXAMPLE 100
6-{2-[N-(3-PHTHALIMIDOPROPYL)-N-n-PROPYLAMINO]ETHYL}-3-OXO-2,3-DIHYDRO-1,4-BENZOXAZINE

EXAMPLE 101
6-{2-[N-(2-PHTHALIMIDOETHYL)AMINO]ETHYL}-3-OXO-2,3-DIHYDRO-1,4-BENZOXAZINE

EXAMPLE 102
6-{2-[N-(2-PHTHALIMIDOETHYL)-N-n-PROPYLAMINO]ETHYL}-3-OXO-2,3-DIHYDRO-1,4-BENZOXAZINE

EXAMPLE 103
3-[4-{N-[2-(3-OXO-2,3-DIHYDRO-1,4-BENZOXAZIN-6-YL) ETHYL] AMINO}BUTYL]-2,4-DIOXO-3-AZASPIRO[4.5]-DECANE

EXAMPLE 104
3-[4-{N-[2-(3-OXO-2,3-DIHYDRO-1,4-BENZOXAZIN-6-YL)-ETHYL]-N-n-PROPYLAMINO{ BUTYL]-BUTYL]-2,4-DIOXO-3-AZASPIRO[4.5]-DECANE

EXAMPLE 105
3-[4-{N-[2-(3-OXO-2,3-DIHYDRO-1,4-BENZOXAZIN-6-YL)-ETHYL] AMINO}BUTYL]-2,4-DIOXO-3-AZABICYCLO[3.3.0]OCTANE

EXAMPLE 106
6-[2-{N-[4-(4,4-DIMETHYL-2,6-DIOXO-1-PIPERIDYL)BUTYL]-AMINO} ETHYL]-3-OXO-2,3-DIHYDRO-1,4-BENZOXAZINE

EXAMPLE 107
6-[2-{N-[4-(4,4-DIMETHYL-2-OXO-1-PIPERIDYL)-BUTYL]AMINO}-ETHYL]-3-OXO-2,3-DIHYDRO-1,4-BENZOXAZINE

EXAMPLE 108
6-[2-{N-[4-(2-OXO-1-PIPERIDYL)BUTYL]AMINO}ETHYL]-3-OXO-2,3-DIHYDRO-1,4-BENZOXAZINE

EXAMPLE 109
6-[2-(N-METHYL-N-CYANOMETHYLAMINO)ETHYL]-3-OXO-2,3-DIHYDRO-1,4-BENZOXAZINE

Using the procedure described in Example 17, but replacing 3-methyl-6-2-(N-methylamino)ethylbenzothiazolinone by 6-2-(N-methylamino)ethyl-3-oxo-2,3-dihydro-1,4-benzoxazine, the product of the title is obtained.

Using the procedure described in Examples 18 and 19 with the product of Example 109, the following are obtained:

EXAMPLE 110
6-{2-[N-PROPYL-N-(2-AMINOETHYL)AMINO]ETHYL}-3-OXO-2,3-DIHYDRO-1,4-BENZOXAZINE

EXAMPLE 111
6-[2-{N-PROPYL-N-[2-(PARA-TOLYLSULFONYLAMINO)ETHYL[AMINO} ETHYL]-3-OXO-2,3-DIHYDRO-1,4-BENZOXAZINE

EXAMPLE 11
6-[2-{N-n-PROPYL-N-[3-(PARA-TOLYLSULFONYLAMINO)PROPYL]-AMINO} ETHYL]-3-OXO-2,3-DIHYDRO-1,4-BENZOXAZINE

Using the procedure described in Example 24, but replacing 3-methyl-6-(2-propylaminoethyl)benzothiazolinone by 6-(2-propylaminoethyl)-3-oxo-2,3-dihydro-1,4-benzoxazine, the product of the title is obtained.

EXAMPLE 113
6-[2-{N-n PROPYL-N-[4-(PARA-TOLYLSULFONYLAMINO)BUTYL]-AMINO} ETHYL] -3-OXO-2,3-DIHYDRO-1,4-BENZOXAZINE

Using the procedure described in Example 112, but replacing 1-chloro-3-bromopropane by 1-chloro-4-bromobutane, the product of the title is obtained.

EXAMPLE 114
3-METHYL-6-[2-{N-[4-(3-OXO-2,3-DIHYDRO-2-BENZISOTHIAZOLYL 1,1DIOXIDE)BUTYL]AMINO}ETHYL]BENZOTHIAZOLINONE

Replacing N-(4-bromobutyl)phthalimide in Example 2 by 3-oxo-2,3-dihydro-2-(4-bromobutyl)beniisothiazole 1,1-dioxide, the product of the title is obtained.

EXAMPLE 115
3-METHYL-6-[2-{N-[4-(3-OXO-2,3-DIHYDRO-2-BENZISOTHIAZOLYL 1,1-DIOXIDE)BUTYL]-N-n-PROPYLAMINO}ETHYL]BENZOTHIAZOLINONE

Using the procedure described in Example 3, but employing the product obtained in Example 114 instead of 3-methyl-6-{2-[N-(4-phthalimidobutyl)amino]ethyl} benzothiazolinone, the product of the title is obtained.

EXAMPLE 116
3-METHYL-6-[2-{N-[3-(3-OXO-2,3-DIHYDRO-2-BENZISOTHIAZOLYL 1,1DIOXIDE)PROPYL]AMINO}ETHYL]BENZOTHIAZOLINONE

By replacing N-(4-bromobutyl)phthalimide in Example 2 by 3-oxo-2,3-dihydro-2-(3-bromopropyl)benzisothiazole 1,1-dioxide, the product of the title is obtained.

EXAMPLE 117

3-METHYL-6-[2-{N-[3-(3-OXO-2,3-DIHYDRO-2-BENZISOTHIAZOLYL 1,1-DIOXIDE)PROPYL]-N-n-PROPYLAMINO}ETHYL]BENZOTHIAZOLINONE

Using the procedure described in Example 3, but employing the product obtained in Example 116 instead of 3-methyl-6-{2-[N- 4-phthalimidobutyl)amino]ethyl} benzothiazolinone, the product of the title is obtained.

EXAMPLE 118

3-METHYL-6-[2-{N-[2-(3-OXO-2,3-DIHYDRO-2-BENZISOTHIAZOLYL 1,1-DIOXIDE)ETHYL]AMINO}ETHYL]BENZOTHIAZOLINONE

By replacing N-(4-bromobutyl)phthalimide in Example 2 by 3-oxo-2,3-dihydro-2-(2-bromoethyl)-benzisothiazole 1,1-dioxide, the product of the title is obtained.

EXAMPLE 119

3-METHYL-6-[2-{N-[2-(3-OXO-2,3-DIHYDRO-2-BENZISOTHIAZOLYL 1,1- DIOXIDE) ETHYL]-N-n-PROPYLAMINO}ETHYL]BENZOTHIAZOLINONE

Using the procedure described in Example 3, but employing the product obtained in Example 118 instead of 3-methyl-6-{2-[N-(4-phthalimidobutyl)amino]ethyl} benzothiazolinone, the product of the title is obtained.

EXAMPLE 120

3-METHYL-6-(4-AMINOBUTYL)BENZOXAZOLINONE (HYDROCHLORIDE)

Using the procedure described in Example 1, but replacing 3-methyl-6-(2-bromoethyl)benzothiazolinone by 3-methyl-6-(4-chlorobutyl)benzothiazolinone, 3-methyl-6-(4-aminobutyl)benzothiazolinone (hydrochloride) is obtained.

EXAMPLES 121 TO 132

Using the procedure described in Examples 2 to 13, but replacing 3-methyl-6-(2-aminoethyl)benzothiazolinone by 3-methyl-6-(4-aminobutyl)benzoxazolinone of Example 120, the following are obtained:

EXAMPLE 121

3-METHYL-6-{4-[N-(4-PHTHALIMIDOBUTYL)AMINO]BUTYL}BENZOXAZOLINONE

EXAMPLE 122

3-METHYL-6-{4-[N-(4-PHTHALIMIDOBUTYL)-N-n-PROPYLAMINO]-BUTYL}BENOXAZOLINONE

EXAMPLE 123

3-METHYL-6-{4-[N-(3-PHTHALIMIDOPROPYL)AMINO]BUTYL}BENOXAZOLINONE

EXAMPLE 124

3-METHYL-6-{4-[N-(3-PHTHALIMIDOPROPYL)-N-PROPYLAMINO]BUTYL}BENOXAZOLINONE

EXAMPLE 125

3-METHYL-6-{4-[N-(2-PHTHALIMIDOETHYL)-N-n-PROPYLAMINO]BUTYL}BENOXAZOLINONE

EXAMPLE 126

3-METHYL-6-{4-[N-(2-PHTHALIMIDOETHYL)AMINO]BUTYL}-BENOXAZOLINONE

EXAMPLE 127

3-[4-{N-[4-(3-METHYLBENZOXAZOLINON-6-YL)BUTYL]AMINO}-BUTYL]-2,4-DIOXO-3-AZASPIRO [4.5]DECANE

EXAMPLE 128

3-[4-{N-[4-(3-METHYLBENZOXAZOLINON-6-YL)BUTYL]N-n-PROPYLAMINO}BUTYL]-2,4-DIOXO-3-AZASPIRO[4.5]DECANE

EXAMPLE 129

3-[4-{N-[4-(3-METHYLBENZOXAZOLINON-6-YL)BUTYL]AMINO}-BUTYL]-2,4-DIOXO-3-AZABICYCLO [3.3.0]OCTANE

EXAMPLE 130

3-METHYL-6-[4-{N-[4-(4,4-DIMETHYL-2,6-DIOXO-1-PIPERIDYL)BUTYL]AMINO}BUTYL]BENZOXAZOLINONE

EXAMPLE 131

3-METHYL-6-[4-{N-[4-(4,4-DIMETHYL-2-OXO-1-PIPERIDYL)BUTYL]AMINO}BUTYL]BENZOXAZOLINONE

EXAMPLE 132

3-METHYL-6-[4-{N-[4-(2-OXO-1-PIPERIDYL)-BUTYL]AMINO}BUTYL]BENZOXAZOLINONE

EXAMPLES 133 TO 144

Using the procedure described in Examples 2 to 13, but replacing 3-methyl-6-(2-aminoethyl)benzothiazolinone by 3-methyl-6-(2-aminoethyl)benzoxazolinone described in Application EP 110,781, the following are obtained:

EXAMPLE 133

3-METHYL-6-{4-[N-(4-PHTHALIMIDOBUTYL)AMINO]ETHYL}BENZOXAZOLINONE

EXAMPLE 134

3-METHYL-6-{4-[N-(4-PHTHALIMIDOBUTYL)-N-n-PROPYLAMINO]ETHYL} BENZOXAZOLINONE

EXAMPLE 135

3-METHYL-6-{4-[N-(3-PHTHALIMIDOPROPYL)AMINO]ETHYL}BENZOXAZOLINONE

EXAMPLE 136

3-METHYL-6-{4-[N-(3-PHTHALIMIDOPROPYL)-N-PROPYLAMINO]ETHYL} BENZOXAZOLINONE

EXAMPLE 137

3-METHYL-6-{4-[N-(2-PHTHALIMIDOETHYL)-N-n-PROPYLAMINO]ETHYL} BENZOXAZOLINONE

EXAMPLE 138

3-METHYL-6-{4-[N-(2-PHTHALIMIDOETHYL)AMINO]ETHYL} BENZOXAZOLINONE

EXAMPLE 139

3-[4-{N-[4-(3-METHYLBENZOXAZOLINON-6-YL)ETHYL]AMINO}BUTYL]-2,4-DIOXO-3-AZASPIRO[4.5]DECANE

EXAMPLE 140

3-[4-{N-[4-(3-METHYLBENZOXAZOLINON-6-YL)ETHYL]-N-n-PROPYLAMINO}BUTYL]-2,4-DIOXO-3-AZASPIRO[4.5]DECANE

EXAMPLE 141

3-[4-{N-[4-(3-METHYLBENZOXAZOLINON-6-YL)ETHYL]AMINO}BUTYL]-2,4-DIOXO-3-AZABICYCLO [3.3.0]OCTANE

EXAMPLE 142

3-METHYL-6-[4-{N-[4-(4,4-DIMETHYL-2,6-DIOXO-1-PIPERIDYL)BUTYL]AMINO}ETHYL]BENZOXAZOLINONE

EXAMPLE 143

3-METHYL-6-[4-{N-[4-(4,4-DIMETHYL-2-OXO-1-PIPERIDYL)-BUTYL] AMINO}ETHYL]BENZOXAZOLINONE

EXAMPLE 144

3-METHYL-6-[4-{N-[4-(2-OXO-1-PIPERIDYL)-BUTYL]AMINO}-ETHYL] BENZOXAZOLINONE

EXAMPLE 145

3-[4-{N-METHYL-N-[2-(3-METHYLBENZOTHIAZOLINON-6-YL)-ETHYL] AMINO}BUTYL]-2,4-DIOXO-3-AZASPIRO[4.5]-DECANE-HYDROCHLORIDE

In a ground-necked flask surmounted by a reflux condenser, $10^{-2}$ mol of 3-methyl-6-[2-(N-methylamino)ethyl]benzoxazolinone, obtained in Example 15, and $1.2 \times 10^2$ mol of triethylamine are dissolved in acetone, and the mixture is brought to reflux for 15 minutes. 0.02 mol of N-(4bromobutyl)-2,4-dioxo-3-azaspiro[4.5]-decane is added and refluxing is maintained for 24 hours. The precipitate formed is drained, the filtrate is evaporated to dryness, the residue is taken up with dilute hydrochloric acid solution, the acidic medium is washed with toluene and then, after alkalinization, the aqueous phase is extracted several times with chloroform.

The organic phases are combined and evaporated to dryness, the residue is taken up with anhydrous ether and the requisite amount of ethereal hydrogen chloride is added. The product is drained, dried and recrystallized.

Yield: 35%
Melting point: 173°-174° C.
Spectral characteristics:
Infrared:
1600–1680 cm$^{-1}$ : v CO
1750 cm$^{-1}$ : v CO (SCON)
1H Nuclear Magnetic Resonance:
2.60 ppm, singlet : 4H 2(NCH$_2$CO)
2.80 ppm, singlet : 3H (amine)
3.50 ppm, singlet : 3H (amide)

EXAMPLE 146

3-[4-{N-METHYL-N-[2-(3-METHYLBENZOTHIAZOLINON-6-YL)-ETHYL-N-METHYLAMINO}BUTYL]-2,4-DIOXO-3-AZABICYCLO[3.3.0]OCTANE HYDROCHLORIDE

Using the procedure described in Example 145, but replacing N-(4-bromobutyl)2,4-dioxo-3-azaspiro4.5decane by N-(4-bromobutyl)-2,4-dioxo-3-azabicyclo-3.3.0octane, the product of the title is obtained.
Yield: 45%
Melting point: 130°-132° C.
Spectral characteristics:
Infrared:
1600–1700 cm$^{-1}$ : v CO
1760 cm$^{-1}$ : v CO (SCON)
1H Nuclear Magnetic Resonance:
2.80 ppm, singlet :3H (CH$_3$)

EXAMPLE 147

3-[4-{N-METHYL-N-[4-(3 METHYLBENZOTHIAZOLINON-6-YL) BUTYL] AMINO}BUTYL]-2,4-DIOXO-3-AZASPIRO[4.5]-DECANE HYDROCHLORIDE

Using the procedure described in Example 145, but replacing 3-methyl-6-2-(N-methylamino)ethylbenzothiazolinone by 3-methyl-6-4-(N-methylamino)butylbenzothiazolinone, obtained in Example 38, the product of the title is obtained.

EXAMPLE 148

3-[4-{N-METHYL-N-[4-(3-METHYLBENZOTHIAZOLINON-6-YL)-BUTYL] AMINO}BUTYL]-2,4-DIOXO-3-AZABICYCLO[3.3.0]OCTANE HYDROCHLORIDE

Using the procedure described in Example 146, but replacing 6-2-(N-methylamino)ethylbenzothiaoxazolinone by 6-[4-(N-methylamino)butylbenzothiazolinone, the product of the title is obtained.

EXAMPLE 149

3-[3-{N-METHYL-N-[2-(3-METHYLBENZO-THIAZOLINON-6-YL)ETHYL]-AMINO} PROPYL]-2,4-DIOXO-3-AZABICYCLO[4.5]DEC-ANE HYDROCHLORIDE

Using the procedure described in Example 145, but replacing N-(4-bromobutyl)-2,4-dioxo-3-azaspiro[4.5]-decane by N-(3-bromopropyl)-2,4-dioxo-3-azaspiro[4.5]-decane, the product of the title is obtained.

EXAMPLE 150

-[3-{N-METHYL-N-[2-(3-METHYLBENZO-THIAZOLINON-6-YL)ETHYL]-AMINO} PROPYL]-2,4-DIOXO-3-AZABICYCLO[3.3.0]OC-TANE HYDROCHLORIDE

Using the procedure described in Example 146, but replacing N-(4-bromobutyl)-2,4-dioxo-3-azabicyclo[3.3.0]-octane by N-(3-bromopropyl)-2,4-dioxo-3-azabicyclo [3.3.0] octane, the product of the title is obtained.

PHARMACOLOGICAL STUDY OF THE COMPOUNDS OF THE INVENTION

EXAMPLE 151

IN VITRO AFFINITY TEST FOR $5\text{-HT}_{1A}$, $D_2$ AND $\alpha_2$ RECEPTORS

The in vitro affinity tests for $5\text{-HT}_{1A}$, $D_2$ and $\alpha_2$ receptors were carried out according to conventional binding techniques.

The results of these studies show that the compounds of the invention possess a K0.5 of the order of $10^{-10}$M with respect to $5\text{-HT}_{1A}$ receptors. This very great affinity is complemented by a very great selectivity. In effect, the ratio of the $5\text{-HT}_{1A}/D_2$ affinities is equal to 100. That of the $5\text{-HT}_{1A}\alpha_2$ affinities is equal to $10^4$.

EXAMPLE 152

ACUTE TOXICITY

The acute toxicity was assessed after oral administration of a dose of 650 mg.kg−1 to batches of 8 mice (26 ±2 grams). The animals were observed at regular intervals during the first day and daily during the two weeks following the treatment.

It is apparent that most of the compounds of the invention are completely non-toxic. Most of them cause no deaths after administration at a dose of 650 mg.kg$^{-1}$, and no disorders are generally observed after administration of this dose.

EXAMPLE 153

STUDY OF ANXIOLYTIC ACTIVITY - PIGEON CONFLICT TEST

Six White Carneaux pigeons not previously used in experiments are trained to peck a Plexiglass key which is transilluminated by red or white lights. The response key is mounted on the front wall of the experimental chamber. The pigeons are brought to 85% of their normal weight before the i0 beginning of the experiment, which is carried out using the method of successive approximations (Frester 1953). At the start, each peck of the key (illuminated with a red or white light) which exceeds a force of 0.15N permits access to a mixture of cereals via an automatic dispenser located under the key. After several days, the cereals are no longer delivered until the thirtieth peck on the key. When this response to the 30th strike is obtained, and when it occurs regularly, permitting the delivery of feed, the color of the light of the key is alternated every three minutes (from white to red and vice versa). The measurement of the level of response to the 30th strike remains operative during each light phase.

During this phase and throughout the experiment, a daily session is composed of 5 cycles of 3 minutes of each light sequence, these sequences being separated by a 30-second interval during which the luminous keys are extinguished and the responses have no effect. Consequently, a sequence lasts approximately 35 to 40 minutes. When these levels of responses are stable and identical for each color during a period of 5 days (this requires 3 to 4 weeks), every 30th response in one of the colored phases simultaneously brings about a release of feed and a brief (200-millisecond) and moderate (1.3 mA) electric shock delivered by electrodes placed on the pubic pones. The level of reponses is reduced at first, then returns to the initial value.

The administration of the products of the invention is carried out after a stable level of response is obtained over a period of 5 days.

The intramuscular injection of the products of the invention at a dose of 0.3 mg/kg$^{-1}$ brings about a significant increase in responses whether or not followed by electric shocks, demonstrating the anxiolytic activity of these products.

EXAMPLE 154

PHARMACEUTICAL COMPOSITIONS

Tablets intended for the treatment of conditions affecting the mind, containing 5 mg of 3-[4-{N-[2-(3-methylbenzothiazolinon-6-yl)ethyl]amino}butyl]-2,4-dioxo-3-azaspiro[4.5]decane.

Preparation formula for 1,000 tablets.

| | |
|---|---|
| 3-[4-{N-[2-(3-Methylbenzothiazolinon-6-yl)ethyl]amino-butyl]-2,4-dioxo-3-azaspiro[4.5]decane | 5 g |
| Wheat starch | 20 g |
| Corn starch | 20 g |
| Lactose | 65 g |
| Magnesium stearate | 2 g |
| Silica | 1 g |
| Hydroxypropylcellulose | 2 g |

Tablets intended for the treatment of pain, containing 2,5 mg of 3-methyl-6-{2-[4-(3-trifluoromethyl-phenyl)-1-piperazinyl]ethyl}benzothiazolinone hydrochloride. Preparation formula for 1,000 tablets

| | |
|---|---|
| 3-Methyl-6-{2-[4-(3-trifluoromethylphenyl)-1-piperazinyl]ethyl}benzothiazolinone hydrochloride | 2,5 g |
| Wheat starch | 15 g |
| Corn starch | 15 g |
| Lactose | 65 g |
| Magnesium stearate | 2 g |
| Silica | 1 g |
| Hydroxypropylcellulose | 2 g |

We claim:

1. A compound selected from these of formula (I):

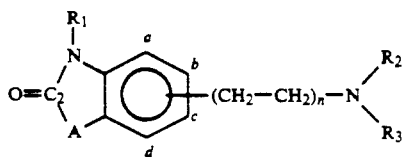

in which:
R₁ represents hydrogen or lower alkyl,
n represents 1 or 2,
A represents oxygen or sulfur,
R₂ represents hydrogen or lower alkyl or lower acyl and R₃ represents (CH₂)pR₄, with p being an integer from 1 to 6 inclusive, and R₄ represents

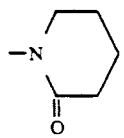

in which:
m is 1 or 2, its enantiomers, diastereoisomers, and epimers as well as its addition salts with a pharmaceutically-acceptable acid or a pharmaceutically-acceptable base when R₁ = H.

2. A compound (I) as claimed in claim 1 in which A represents an oxygen atom, its enantiomers, epimers and diastereoisomers as well as its addition salts with a pharmaceutically-acceptable acid or a pharmaceutically-acceptable base when R₁ = H.

3. A compound (I) as claimed in claim 1 in which A represents a sulfur atom, its enantiomers, epimers and diastereoisomers as well as its addition salts with a pharmaceutically-acceptable acid or a pharmaceutically-acceptable base when R₁ = H.

4. A compound as claimed in claim 1 in which the group (CH₂—CH₂)ₙ—NR₂R₃ is at position b, its enantiomers, epimers and diastereoisomers as well as its addition salts with a pharmaceutically acceptable acid or a pharmaceutically-acceptable base when R₁ = H.

5. A compound (I) as claimed in claim 1 in which the group (CH₂—CH₂)ₙ—NR₂R₃ is at position c, its enantiomers, epimers and diastereoisomers as well as its addition salts with a pharmaceutically-acceptable acid or a pharmaceutically-acceptable base when R₁ = H.

6. A compound (I) as claimed in claim 1 in which the group (CH₂—CH₂)ₙ—NR₂R₃ is at position d, its enantiomers, epimers and diastereoisomers as well as its addition salts with a pharmaceutically-acceptable acid or a pharmaceutically-acceptable base when R₁ = H.

7. A compound (I) as claimed in claim 1 selected from those in which A represents a sulfur atom, n is equal to 1 and R₃ represents a group (CH₂)pR₄, with p being 1 to 6, inclusive and R₄ represents

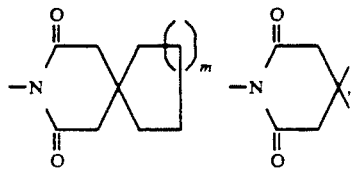

in which m is 1 or 2, its enantiomers, epimers and diastereoisomers as well as its addition salts with a pharmaceutically-acceptable acid or a pharmaceutically-acceptable base when R₁ = H.

8. A compound as claimed in claim 1 which is selected from 3-[4-{N-[2-(3-methylbenzothiazolin-2)on-6yl)ethyl[amino}-butyl]-2,4-dioxo-3-azaspiro [4.5]decane, as well as its addition salts with a pharmaceutically-acceptable acid.

9. A compound which is selected from 3-methyl6-[2-{N-[4-(4,4-dimethyl-2,6-dioxo-1-piperidyl)-butyl-]amino} ethyl]benzothiazolinone, as well as its addition salts with a pharmaceutically-acceptable acid.

10. A pharmaceutical composition containing as active principle an effective antidepressive or anxiolytic amount of a 5HT1A agonist, being at least one compound as claimed in claim 1, in combination with one or more pharmaceutically-acceptable excipients or vehicles.

11. A method of treating a mammal afflicted with a disease requiring for its treatment an antidepressive or anxiolytic amount of a 5HT1A receptor agonist comprising the step of administering to the said mammal an amount of a compound of claim 1 which is effective for alleviation of the said disease.

* * * * *

UNITED STATES PATENT AND TRADEMARK OFFICE
CERTIFICATE OF CORRECTION

PATENT NO. : 5,196,434

DATED : Mar. 23, 1993

INVENTOR(S) : Thierry Taverne, Isabelle Lesieur, Patrick Depreux, Daniel H. Caignard, Béatrice Guardiola, Gérard Adam, Pierre Renard Page 1 of 7

It is certified that error appears in the above-indentified patent and that said Letters Patent is hereby corrected as shown below:

Column 3, line 68; "acid or" should read -- acid or base. --.
Column 5, line 40; "have the as" should read -- have the same definition as --.
Column 10, approximately line 14; "-6-2-N-" should read -- -6-[2-[N- --.
Column 10, approximately line 15; move the closing parenthesis from the beginning of line 15 to the end of line 14 before the hyphen.
Column 10, approximately line 15; "AMINOETHYL)" should read -- AMINO]ETHYL} --.
Column 10, line 46/47; move the closing parenthesis from the beginning of line 47 to the end of line 46 before the hyphen.
Column 11, approximately line 58/59; move the closing parenthesis from the beginning of line 59 to the end of line 58 before the hyphen.
Column 12, line 48; "$cm^{-1}$ v CH" should read -- $ch^{-1}$: v CH --.
Column 14, line 11; "50 mol" should read -- 50 ml --.
Column 14, line 30; "ETHYL AMINO]" should read -- ETHYL) AMINO]--.
Column 15, line 53; move the closing parenthesis from the beginning of line 53 to the end of line 52 before the hyphen.
Column 15, line 64; move the "e" at the end of line 64 to the beginning of line 65 before "thyl".
Column 17, approximately line 13; move the closing parenthesis from the beginning of line 13 to the end of line 12 before the hyphen.
Column 17, approximately line 28; move the closing parenthesis from the beginning of line 28 to the end of line 27 before the hyphen.
Column 17, line 38; "[4.51]-" should read -- [4.5] --.
Column 18, approximately line 12; "-6-4-(N-" should read -- -6-[4-(N-" --
Column 18, approximately line 13; "butylbenzothiazolinone," should read -- butyl]benzothiazolinone, --.
Column 18, approximately line 45; "-N-2-" should read -- -N-[2- --.

UNITED STATES PATENT AND TRADEMARK OFFICE
CERTIFICATE OF CORRECTION

PATENT NO. : 5,196,434  
DATED : Mar. 23, 1993  
INVENTOR(S) : Thierry Taverne, Isabelle Lesieur, Patrick Depreux, Daniel H. Caignard, Béatrice Guardiola, Gerard Adam Pierre, Renard It is certified that error appears in the above-indentified patent and that said Letters Patent is hereby corrected as shown below:

Column 19, approximately line 9; move the "E" at the end of line 8 to the beginning of line 9 and insert before "THYL".

Column 19, line 17; move the "E" at the end of line 18 to the beginning of line 19 and insert before "THYL".

Column 19, approximately line 27; move the closing bracket from the beginning of line 27 to the end of line 26 and insert after "ETHYL".

Column 19, line 31; "3-[4-[(N-" should read --3-[4- [N- --.

Column 19, line 31/32; move the "E" at the end of line 31 to the beginning of line 32 and insert before "THYL".

Column 19, line 32/33; move "O" from the beginning of line 33 to the end of line 32 and insert after "DIOX".

Column 19, line 52; move the closing bracket from the beginning of line 52 to the end of line 51 and insert after "BUTYL".

Column 19, approximately line 55,56; move the closing bracket from the beginning of line approximately 52 to the end of line 51 and insert before the hyphen.

Column 19, line 55/56; move the "4" from line 55 to the beginning of line 56 and insert a hyphen thereafter.

Column 19, line 55/56; move the "4" from line 55 to the beginning of line 56 and insert a hyphen("-")thereafter Column 19, line 56; "ETHYL" should read -- METHYL --.

Column 20, line 4; move the closing parenthesis from the beginning of line 4 to the end of line 3 and insert before the hyphen.

Column 20, lines 13/14; move the closing parenthesis from the beginning of line 14 to the end of line 13 and insert before the hyphen.

Column 20, lines 23/24; move the closing parenthesis from the beginning of line 24 to the end of line 23 and insert before the hyphen.

Column 20, approximately line 33; "-DIHYDRO 3-OXO" should read -- -DIHYDRO-3-OXO- --.

UNITED STATES PATENT AND TRADEMARK OFFICE
CERTIFICATE OF CORRECTION

PATENT NO. : 5,196,434

DATED : Mar. 23, 1993

INVENTOR(S) : Thierry Taverne, Isabelle Lesieur, Patrick Depreux, Daniel H. Caignard, Béatrice Guardiola, Gérard Adam Pierre Renard It is certified that error appears in the above-indentified patent and that said Letters Patent is hereby corrected as shown below:

Column 20, approximately line 41; move the "O" at the beginning of line 40 to the end of line 40 and insert before the hyphen.
Column 20, approximately line 45; "N-4-" should read --N-[4- --.
Column 21, line 6; "OXO1,4-" should read -- -OXO-1,4- --.
Column 21, line 29; "-6-2-" should read -- -6-[2- --.
Column 21, line 29; "ethylbenzo-" should read --ethyl]zenzo- --
Column 21, line 30; "-7-4-" should read -- -7-[4- --.
Column 21, line 54/55; "but i5 replacing" should read
   -- but replacing --.
Column 21, line 57; "1,4benzoxazine," should read
   -- 1,4-benzoxazine, --.
Column 22, line 50; "1,4BENZOXAZINE" should read
   -- 1,4-BENZOXAZINE --.
Column 22, line 56; "1,4benzoxazine," should read
   -- 1,4-benzoxazine, --.
Column 22, line 65; "1,4benzoxazine" should read
   -- 1,4-benzoxazine --.
Column 23, line 3; move the closing parenthesis ")" from the
   beginning of line 4 to the end of line 3 and insert before
   the hyphen.
Column 23, line 8; move the hyphen "-" from the beginning of line
   9 to the end of line 8 and insert after "L".
Column 23, line 24; move the closing parenthesis ")" from the
   beginning of approximately line 23 to the end of line 22 and
   insert before the hyphen.
Column 23, approximately line 68; "-6-2-" should read -- -6-[2- --.
Column 23, approximately line 68; "ethylbenzo-" should read
   -- ethyl]benzo- --.
Column 24, line 1; "ethyl-3-" should read -- ethyl]-3- --.
Column 24, line 2; "1,4benzoxazine," should read
   -- 1,4-benzoxazine, --.
Column 24, line 16; move "E" to the beginning of line 17 and
   insert before "THYL".

UNITED STATES PATENT AND TRADEMARK OFFICE
CERTIFICATE OF CORRECTION

PATENT NO. : 5,196,434

Page 4 of 7

DATED : Mar. 23, 1993

INVENTOR(S) : Thierry Taverne, Isabelle Lesieur, Partric Depreaux, Daniel H. Caignard, Béatrice Guardiola, Gérard Adam Pierre Renard It is certified that error appears in the above-indentified patent and that said Letters Patent is hereby corrected as shown below:

Column 24, line 20; "-[2≡N-" should read -- [2-{N- --.
Column 24, line 32: "N-{4-" should read -- N-[4- --.
Column 24, line 48; delete "i5".
Column 25, line 5; move the "E" from the end of line 5 to the beginning of line 6 and insert before "THYL".
Column 25, line 6; "1,4BENZOXAZINE" should read --
-- 1,4-BENZOXAZINE --.
Column 25, line 14; move the "E" from the end of line 14 to the beginning of line 15 and insert before "THYL".
Column 25, line 15; "1,4BENZOXAZINE" should read
-- 1,4-BENZOXAZINE --.
Column 25, approximately line 23; move the "E" from the end of line 23 to the beginning of line 24 and insert before "THYL".
Column 25, line 39/40; change the "{" to --}-- and move from the end of line 39 to the beginning of line 40 and insert before "BUTYL".
Column 25, approximately line 40; delete "BUTYL]-", second occurrence.
Column 25, approximately line 61; move the closing bracket "]" from the beginning of line 61 to the end of line 60 and insert before the hyphen.
Column 25, lines 65/66; move the "E" from the end of line 65 to the beginning of line 66 and insert before "THYL".
Column 25, last line; "ethylbenzo-" should read --ethyl]benzo- --.
Column 26, line 1; "6-2-" should read -- 6-[2- --.
Column 26, line 1; "ethyl-3-" should read -- ethyl]-3- --.
Column 26, line 10; move the "E" from the end of line 10 to the beginning of line 11 and insert before "THYL".
Column 26, line 16; "ETHYL[AMINO}" should read --ETHYL]AMINO} --.
Column 26, line 20; "EXAMPLE 11" should read --EXAMPLE 112 --.
Column 26, line 44; "1,1DIOXIDE" should read -- 1,1-DIOXIDE --.
Column 26, line 53; move the "E" from the end of line 53 to the beginning of line 54 and insert before "THYL".

UNITED STATES PATENT AND TRADEMARK OFFICE
CERTIFICATE OF CORRECTION

PATENT NO. : 5,196,434
DATED : Mar. 23, 1993
INVENTOR(S) : Thierry Taverne, Isabelle Lesieur, Patrick Depreux, Daniel H. Caignard, Béatrice Guardiola, Gérard Adam, Pierre Renard It is certified that error appears in the above-indentified patent and that said Letters Patent is hereby corrected as shown below:

Column 26, line 64; "1,1DIOXIDE)" should read -- 1,1-DIOXIDE) --.
Column 27, approximately line 7; move the "E" from the end of approximately line 7 to the beginning of line 8 and insert before "THYL".
Column 28, line 5; move the closing parenthesis ")" from the beginning of line 5 to the end of line 4 and insert before the hyphen.
Column 28, lines 10, 15, 19-20, 24-25, and 30; in each instance, "BENOXAZOLINONE" should read -- BENZOXAZOLINONE --.
Column 28, lines 5, 15, 30, in each instance, move the closing parenthesis ")" from lines 5, 15, 30, to the previous lines in each instance, and insert before the hyphen.
Column 28, line 50; move the "O-" from line 50 to the end of line 49 and insert before the hyphen.
Column 29, lines 4 and approximately 13, in each instance move the closing parenthesis ")" from lines 4 and 13 to lines 3 and 12 and insert before the hyphen in each instance.
Column 29, line 26; move the "E" from the end of line 26 to the beginning of line 27 and insert before "THYL".
Column 29, line 30; "N-[4" should read -- N-[4- --.
Column 29, lines 45/46; move the "O" from the beginning of line 46 to the end of line 45 before the hyphen.
Column 29, approximately line 68; "1.2X10$^2$" should read -- 1.2 x 10$^{-2}$ --.
Column 30, line 1; "N-4bromobutyl)" should read -- N-(4-bromobutyl) --.
Column 30, line 35/36; "azaspiro4.5dec-" should read -- azaspiro[4.5]dec- --.
Column 30, line 37; "3.3.0 octane," should read -- [3.3.0]octane, --.
Column 30, line 49; "-N-[4-(3" should read -- -N-[4-(3- --.
Column 30, line 50; "-6-YL)BUTYL]" should read -- -6-YL)-BUTYL] --.
Column 30, line 56; "-6-4-" should read -- -6-[4- --.
Column 30, line 56; "butyl-" should read -- butyl]- --.

UNITED STATES PATENT AND TRADEMARK OFFICE
CERTIFICATE OF CORRECTION

PATENT NO. : 5,196,434
DATED : Mar. 23, 1993
INVENTOR(S) : Thierry Taverne, Isabelle Lesieur, Patrick Depreux, Daniel H. Caignard, Béatrice Guardiola, Gerard Adam, Pierre Renard It is certified that error appears in the above-indentified patent and that said Letters Patent is hereby corrected as shown below:

Column 30, page 66; "6-2-" should read -- 6-[2- --.
Column 30, line 66; "ethylbenzothiaoxazoli-" should read
  -- ethyl]benzothiaoxazoli --.
Column 30, line 67; "butylbenzothiazolinone," should read
  -- butyl]benzothiazolinone, --.
Column 31, approximately line 14; "-[3-" should read -- 3-[3- --.
Column 31, line 38; "5-HT$_{1A}$α2" should read --5-HT$_{1A}$/α2 --.
Column 31, approximately line 63; delete "i0".
Column 32, approximately line 68; "these" should read -- those--.
  (PA 9-11-91, P. 1)
Column 33, approximately line 15; after "represents" insert
  -- any one of the following groups: --.
Column 33, line 16; insert above the formula:

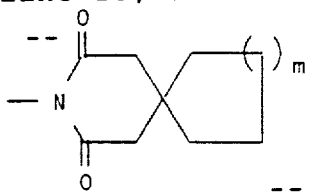   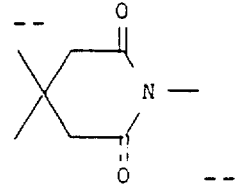

Column 33, line 23; insert below the formula:

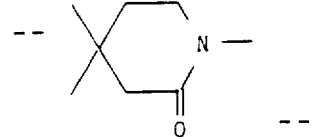

Column 33, approximately line 29; delete "(I)". (Cl. 2, old Cl. 4,

Column 33, approximately line 34; delete "(I)".(Cl. 3, old Cl. 5,

Column 33, approximately line 42; "pharmaceutically acceptable"
  should read -- pharmaceutically-acceptable --.(Cl. 4, old Cl. 8,

UNITED STATES PATENT AND TRADEMARK OFFICE
CERTIFICATE OF CORRECTION

PATENT NO. : 5,196,434
DATED : Mar. 23, 1993
INVENTOR(S) : Thierry Taverne, Isabelle Lesieur, Patrick Depreux, Daniel H. Caignard, Béatrice Guardiola, Gérard Adam, Pierre Renard It is certified that error appears in the above-indentified patent and that said Letters Patent is hereby corrected as shown below:

Column 33, approximately line 44; delete "(I)".

Column 34, line 1; delete "(I)".

Column 34, approximately line 7; delete "(I)".

Column 34, line 10; insert after "represents" -- one of the following groups:

Column 34, line 26; "(3-methylbenzothiazolin-2)" should read -- (3-methylbenzothiazolin-2- --.

Column 34, line 27; "6yl)ethyl[" should read -- 6-yl)ethyl] --.

Column 34, line 31; "-methyl6-" should read -- -methyl-6- --.

Column 34, line 33; move the closing bracket "]" from the beginning of line approximately 33 to the end of line 32 and insert before the hyphen "-".

Signed and Sealed this

Fifteenth Day of March, 1994

Attest:

BRUCE LEHMAN

*Attesting Officer*   *Commissioner of Patents and Trademarks*